(12) United States Patent
Zhang et al.

(10) Patent No.: US 8,957,236 B2
(45) Date of Patent: Feb. 17, 2015

(54) COMPOUND AND ORGANIC DEVICE EMPLOYING SAME

(75) Inventors: Qisheng Zhang, Fukuoka (JP); Chihaya Adachi, Fukuoka (JP); Shigeyuki Matsunami, Fukuoka (JP); Kei Sakanoue, Fukuoka (JP)

(73) Assignee: Kyushu University National University Corporation, Fukuoka (JP)

( * ) Notice: Subject to any disclaimer, the term of this patent is extended or adjusted under 35 U.S.C. 154(b) by 0 days.

(21) Appl. No.: 14/128,665

(22) PCT Filed: Jun. 22, 2012

(86) PCT No.: PCT/JP2012/065955
§ 371 (c)(1),
(2), (4) Date: Dec. 23, 2013

(87) PCT Pub. No.: WO2012/176864
PCT Pub. Date: Dec. 27, 2012

(65) Prior Publication Data
US 2014/0135530 A1    May 15, 2014

(30) Foreign Application Priority Data

Jun. 24, 2011  (JP) .................................. 2011-140046
Jun. 24, 2011  (JP) .................................. 2011-140047

(51) Int. Cl.
| | | |
|---|---|---|
| C07F 9/53 | (2006.01) | |
| H01L 51/00 | (2006.01) | |
| C07F 9/50 | (2006.01) | |
| C07F 9/572 | (2006.01) | |
| C07F 9/58 | (2006.01) | |
| C07F 9/655 | (2006.01) | |
| C07F 9/6553 | (2006.01) | |
| C07F 15/00 | (2006.01) | |
| C09K 11/06 | (2006.01) | |
| H05B 33/14 | (2006.01) | |
| H01L 51/50 | (2006.01) | |

(52) U.S. Cl.
CPC ............ *H01L 51/005* (2013.01); *C07F 9/5045* (2013.01); *C07F 9/5325* (2013.01); *C07F 9/5329* (2013.01); *C07F 9/5728* (2013.01); *C07F 9/582* (2013.01); *C07F 9/65517* (2013.01); *C07F 9/655354* (2013.01); *C07F 15/0033* (2013.01); *H01L 51/009* (2013.01); *H01L 51/0091* (2013.01); *C09K 11/06* (2013.01); *H05B 33/14* (2013.01); *H01L 51/0085* (2013.01); *H01L 51/5016* (2013.01); *C09K 2211/1007* (2013.01); *C09K 2211/1014* (2013.01); *H01L 51/5072* (2013.01)
USPC .................................. 556/404; 568/14; 568/15

(58) Field of Classification Search
USPC ....................... 568/14, 15; 556/404
See application file for complete search history.

(56) References Cited

U.S. PATENT DOCUMENTS

| | | | |
|---|---|---|---|
| 2007/0087219 | A1 | 4/2007 | Ren et al. |
| 2007/0290605 | A1 | 12/2007 | Goto et al. |
| 2013/0295706 | A1 | 11/2013 | Goto et al. |

FOREIGN PATENT DOCUMENTS

| | | | |
|---|---|---|---|
| CN | 101747374 A | | 6/2010 |
| JP | 3261791 A | | 11/1991 |
| JP | 2000133453 A | | 5/2000 |
| JP | 201193825 A | | 5/2011 |
| JP | 2011100943 A | | 5/2011 |
| JP | 2011190239 A | | 9/2011 |
| JP | 2012193352 A | | 10/2012 |
| WO | 2005104628 A1 | | 11/2005 |
| WO | 2006130353 A2 | | 12/2006 |
| WO | 2010046259 A1 | | 4/2010 |
| WO | 2010137779 A1 | | 12/2010 |
| WO | 2011070963 A1 | | 6/2011 |

OTHER PUBLICATIONS

D. Zhao, et al, "Preparation of new C2-symmetric tetraphosphine ligands for Rh-catalyzed asymmetric hydrogenation of arylenamides", Tetrahedron Letters, vol. 48, No. 29, p. 5095-5098 (2007).

(Continued)

*Primary Examiner* — Porfirio Nazario Gonzalez
(74) *Attorney, Agent, or Firm* — Browdy and Neimark, PLLC

(57) ABSTRACT

The compounds represented by the following general formula have excellent properties as a charge transport material. In the formula, $R^1$ to $R^3$ represent a substituent, n1 and n2 indicate an integer of from 0 to 5, n3 indicates an integer of from 0 to 4, X represents a linking group of —O—, —S—, —SO$_2$—, —CS—, —R$^4$—, —C(R$^5$)(R$^6$)—, —PO(R$^7$)—, —Si(R$^8$)(R$^9$)—, >PO—, >Si(R$^{10}$)— or >Si<, m is an integer of from 2 to 4, $R^4$ represents an aliphatic cyclic linking group, and $R^5$ to $R^{10}$ represent a hydrogen atom, an alkyl group, an aryl group, etc.

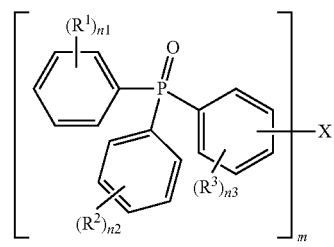

12 Claims, 3 Drawing Sheets

(56) References Cited

OTHER PUBLICATIONS

J. Ivar van der Vlugt, et al, "New Diphosphane Ligands Based on Bisphenol A Backbones—Synthesis and Coordination Chemistry" European Journal of Inorganic Chemistry, No. 24, p. 4361-4369 (2003).

W. Adam, et al, "Electronic substituent effeds in radical chemistry . . . ", Anales de Quimica International edition, vol. 37, No. 4, p. 271-276 (1997).

N. Morohashi, et al, "Synthesis of a Sulfur-bridged Diphosphine Ligand and Its Unique Complexation Properties toward Palladium(II) Ion" Chemistry Letters, vol. 37, No. 4, p. 418-419 (2008).

Y. Akahira, et al, "Synthesis of novel dihydroxydiphosphines and dibydroxydicarboxylic acids having a tetra(thio-1,3-phenylene-2-yl) backbone" Supramolecular Chemistry, vol. 23, No. 1-2, p. 144-155 (2011).

L. Xiao, et al "Recent Progresses on Materials for Electrophosphorescent Organic Light-Emitting Devices" Advanced Materials, vol. 23, p. 926-952 (2011).

P.A. Vecchi et al., "A Dibenzofuran-Based Host Material for Blue Electrophosphorescence", Organic Letters, vol. 8, No. 19, p. 4211-4214 (2006).

S.O. Jeon, "External Quantum Effi ciency Above 20% in Deep Blue Phosphorescent Organic Light-Emitting Diodes" Advanced Matter, p. 1436-1441 (2011).

C. Han, "A Simple Phosphine—Oxide Host with a Multi-insulating Structure: High Triplet Energy Level for Efficient Blue Electrophosphorescence" Chemistry European Journal, vol. 17, p. 5800-5803 (2011).

A. L. Von Ruden, "Phosphine Oxide Based Electron Transporting and Hole Blocking Materials for Blue Electrophosphorescent Organic Light Emitting Devices", Chem. Mater., 22, p. 5678 (2010).

International preliminarnary report on patentability in connection with corresponding PCT | J P20121065955, mailed Jun. 22, 2012.

Japanese Office Action dated Aug. 19, 2014, issued in connection with corresponding Application No. 2011-140046.

COMPOUND AND ORGANIC DEVICE EMPLOYING SAME

TECHNICAL FIELD

The present invention relates to a novel compound useful as a charge transport material, and to an organic device such as an organic electroluminescence element (organic EL element) using the compound.

BACKGROUND ART

A lot of studies for increasing the luminescent efficiency of organic electroluminescence elements are being made. Up to now, various kinds of efforts have been made to increase the luminescent efficiency by newly developing and combining an electron transport material, a hole transport material, a light-emitting materials and others that constitute an organic electroluminescence element. Above all, a phosphorescent material can use the excited triplet state thereof and has a high quantum efficiency, and is therefore specifically noted as a light-emitting material. However, the phosphorescent material has a common challenge in that it readily undergoes triplet-triplet deactivation, and therefore, for preventing such deactivation, various investigation have been made (see NPL 1).

A compound having a triphenylphosphine oxide structure has a high lowest excited triplet energy level as compared with conventional carbazole compounds, and is therefore specifically noted as a host material for light-emitting materials. For example, PTL 1 says that selective use of a compound having a lowest excited triplet energy level of not lower than 2.65 eV could improve a luminescent efficiency, describing an organic electroluminescence element that has a configuration where a layer of a compound having the following structure and doped with a light-emitting material is laminated on a layer of 4,4'-bis[N-(1-naphthyl)-N-phenylamino]biphenyl (NPB).

[Chem. 1]

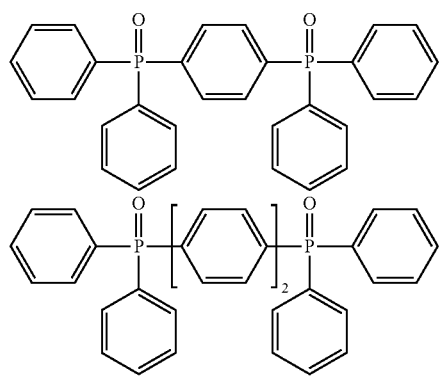

NPL 2 describes an organic electroluminescence element that has a configuration where a hole transport layer formed of 4,4',4''-tris(carbazol-9-yl)triphenylamine (TCTA) is laminated on a light-emitting layer of a compound having the following triphenylphosphine oxide structure and doped with iridium (III) bis(4,6-difluorophenyl)pyridinato-N,$C^2$)picolinate (FIrpic).

[Chem. 2]

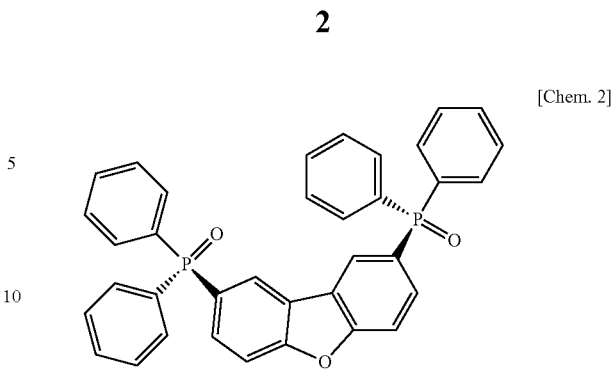

NPL 3 describes an organic electroluminescence element that has a configuration where a light-emitting layer of 9-(3-(9H-carbazol-9-yl)phenyl)-3-(dibromophenylphosphoryl)-9H-carbazole (mCPPO1) doped with bis(3,5-difluoro-4-cyanophenyl)pyridine) iridium picolinate (FCONIrpic) is laminated on a layer formed of a compound having the following triphenylphosphine oxide structure. This reference says that the organic electroluminescence element having the configuration can attain a high luminescent efficiency.

[Chem. 3]

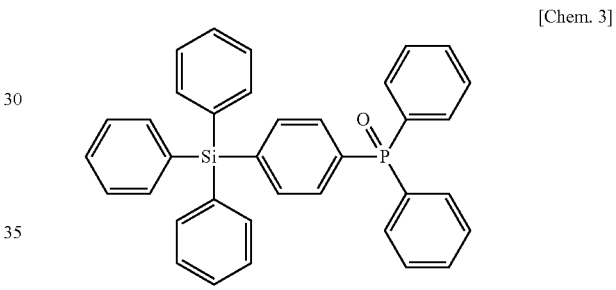

NPL 4 describes an organic electroluminescence element that has a configuration where a light-emitting layer of a compound having the following triphenylphosphine oxide structure and doped with iridium(III) bis(4,6-difluorophenyl)pyridinato-N,$C^2$)picolinate (FIrpic) is laminated with a hole transport layer formed of 4,4',4''-tris(carbazol-9-yl)triphenylamine (TCTA). This reference says that the organic electroluminescence element having the configuration can attain a high luminescent efficiency.

[Chem. 4]

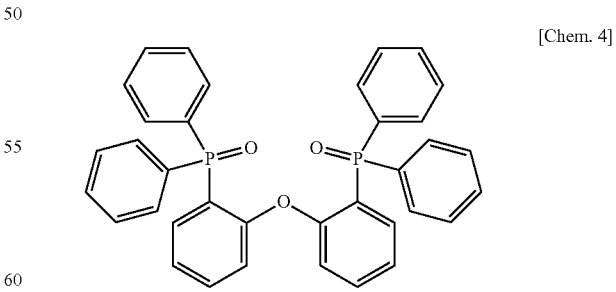

NPL 5 describes a compound having the following triphenylphosphine oxide structure. This reference further describes an organic electroluminescence element that uses the compound having such a triphenylphosphine oxide structure as the electron transport material therein.

[Chem. 5]

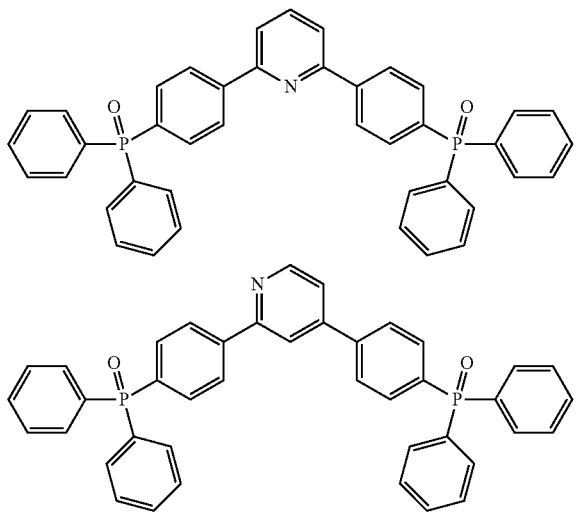

CITATION LIST

Patent Literature

PTL 1: WO2006/130353

Non-Patent Literature

NPL 1: L. Xiao, Adv. Mater. 2011, 23, 926-952
NPL 2: P. A. Vecchi, et. al., Organic Letters, 2006, Vol. 8, No. 19, 4211-4214
NPL 3: S. O. Jeon, Adv. Mater. 2011, XX, 1-6
NPL 4: C. Han, Chem. Eur. J. 2011, 17, 5800-5803
NPL 5: Chem. Mater., 2010, 22, 5678

SUMMARY OF INVENTION

Technical Problem

As in the above, various investigations have heretofore been made relating to compounds that contain a triphenylphosphine oxide structure. However, it could not be said that comprehensive studies would have been made relating to all compounds that contain a triphenylphosphine oxide structure. In addition, there has not as yet been found out any distinct relationship between the chemical structure of the compounds containing a triphenylphosphine oxide structure and the usefulness of the compounds as an electronic device material, and the current situation is that the usefulness of the compounds as an electronic device material on the basis of the chemical structure thereof is difficult to predict. Further, synthesis of the compounds that contain a triphenylphosphine oxide structure is not always easy, and therefore it is often difficult just to provide the compounds. Given the situation, the present inventors have tried to synthesize novel compounds having a triphenylphosphine oxide structure that have not as yet been developed in the art, and have investigated evaluating the usefulness of the synthesized novel compounds as an electronic device material. Specifically, the present inventors have made assiduous studies, having an objective of providing novel compounds that contain a triphenylphosphine oxide structure and are useful as an electronic device material.

Solution to Problem

For solving the above-mentioned problems, the present inventors have made assiduous studies and, as a result, have found that novel compounds having a specific structure including a triphenylphosphine oxide structure have excellent properties as an electronic device material. Based on this finding, the present inventors have provided the present invention described hereinunder, as a solution to the above problems.

[1] A compound represented by the following general formula (1):

General Formula (1)

[Chem. 6]

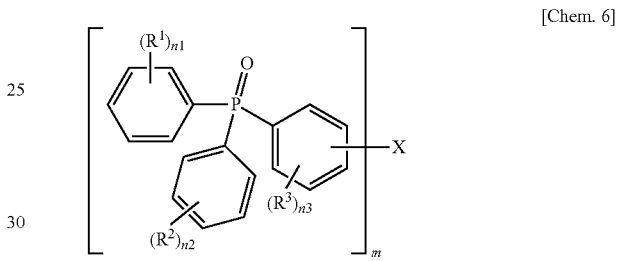

[In the general formula (1), $R^1$, $R^2$ and $R^3$ each independently represent a substituent, n1 and n2 each independently indicate an integer of from 0 to 5, n3 indicates an integer of from 0 to 4, X represents a linking group having any of the following structures, m is equal to the valence of the linking group X and indicates an integer of from 2 to 4.

[Chem. 7]

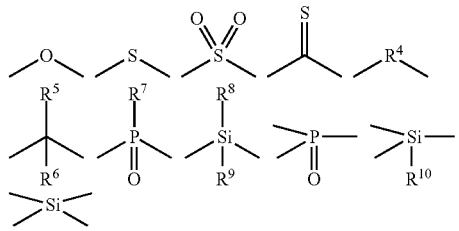

In the above-mentioned structures of the linking group, $R^4$ represents a substituted or unsubstituted aliphatic cyclic linking group. $R^5$ and $R^6$ each independently represent a hydrogen atom, a halogen atom, a substituted or unsubstituted alkyl group, or a substituted or unsubstituted aryl group. $R^7$, $R^8$, $R^9$ and $R^{10}$ each independently represent a hydrogen atom, a substituted or unsubstituted alkyl group, or a substituted or unsubstituted aryl group. At least one of $R^8$ and $R^9$ is a hydrogen atom, or a substituted or unsubstituted alkyl group.

However, when X is —O— or —($R^7$)P(=O)—, this links at the 3,3'-positions of the triphenylphosphine oxide structure of the general formula (1). When X is >PO—, this links at the 3,3',3"-positions of the triphenylphosphine oxide structure of the general formula (1).]

[2] A compound represented by the following general formula (2):

General Formula (2)

[Chem. 8]

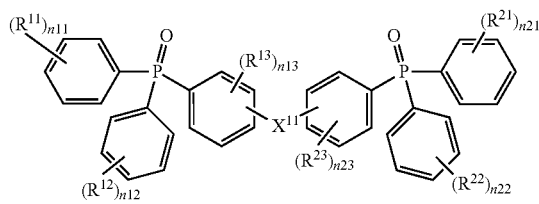

[In the general formula (2), $R^{11}$, $R^{12}$, $R^{13}$, $R^{21}$, $R^{22}$ and $R^{23}$ each independently represent a substituent, n11, n12, n21 and 1 n22 each independently indicate an integer of from 0 to 5, n13 and n23 each independently indicate an integer of from 0 to 4, $X^{11}$ represents a linking group having any of the following structures.

[Chem. 9]

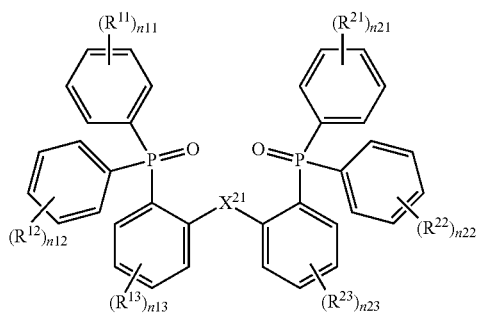

In the above-mentioned structures of the linking group, $R^4$ represents a substituted or unsubstituted aliphatic cyclic linking group. $R^5$ and $R^6$ each independently represent a hydrogen atom, a halogen atom, a substituted or unsubstituted alkyl group, or a substituted or unsubstituted aryl group. $R^7$, $R^8$, $R^9$ and $R^{10}$ each independently represent a hydrogen atom, a substituted or unsubstituted alkyl group, or a substituted or unsubstituted aryl group. At least one of $R^8$ and $R^9$ is a hydrogen atom, or a substituted or unsubstituted alkyl group.

However, when X is —O— or —($R^7$)P(=O)—, this links at the 3,3'-positions of the triphenylphosphine oxide structure of the general formula (1).]

[3] A compound represented by the following general formula (2-1):

General Formula (2-1)

[Chem. 10]

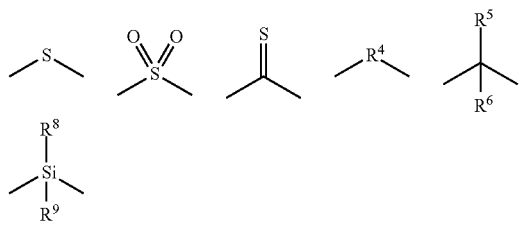

In the general formula (2-1), $R^{11}$, $R^{12}$, $R^{13}$, $R^{21}$, $R^{22}$ and $R^{23}$ each independently represent a substituent, n11, n12, n21 and n22 each independently indicate an integer of from 0 to 5, n13 and n23 each independently indicate an integer of from 0 to 4, $X^{21}$ represents a linking group having any of the following structures.

[Chem. 11]

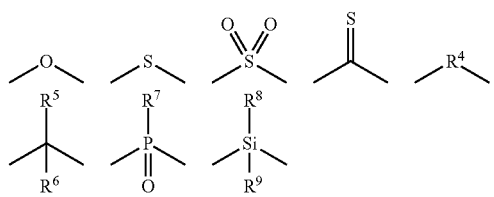

In the above-mentioned structures of the linking group, $R^4$ represents a substituted or unsubstituted aliphatic cyclic linking group. $R^5$ and $R^6$ each independently represent a hydrogen atom, a halogen atom, a substituted or unsubstituted alkyl group, or a substituted or unsubstituted aryl group. $R^7$, $R^8$ and $R^9$ each independently represent a hydrogen atom, a substituted or unsubstituted alkyl group, or a substituted or unsubstituted aryl group. At least one of $R^8$ and $R^9$ is a hydrogen atom, or a substituted or unsubstituted alkyl group.]

[4] A compound represented by the following general formula (2-2):

General Formula (2-2)

[Chem. 12]

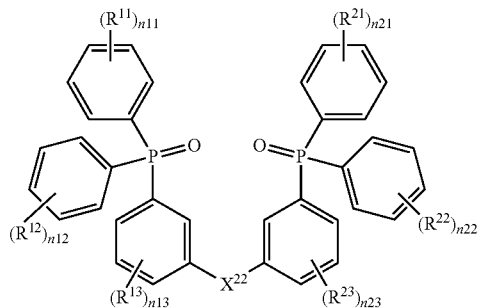

[In the general formula (2-2), $R^{11}$, $R^{12}$, $R^{13}$, $R^{21}$, $R^{22}$ and $R^{23}$ each independently represent a substituent, n11, n12, n21 and n22 each independently indicate an integer of from 0 to 5, n13 and n23 each independently indicate an integer of from 0 to 4, $X^{22}$ represents a linking group having any of the following structures.

[Chem. 13]

In the above-mentioned structures of the linking group, $R^4$ represents a substituted or unsubstituted aliphatic cyclic linking group. $R^5$ and $R^6$ each independently represent a hydrogen atom, a halogen atom, a substituted or unsubstituted alkyl group, or a substituted or unsubstituted aryl group. $R^7$, $R^8$ and $R^9$ each independently represent a hydrogen atom, a substituted or unsubstituted alkyl group, or a substituted or unsubstituted aryl group. At least one of $R^8$ and $R^9$ is a hydrogen atom, or a substituted or unsubstituted alkyl group.]

[5] A compound represented by the following general formula (2-3):

General Formula (2-3)

[Chem. 14]

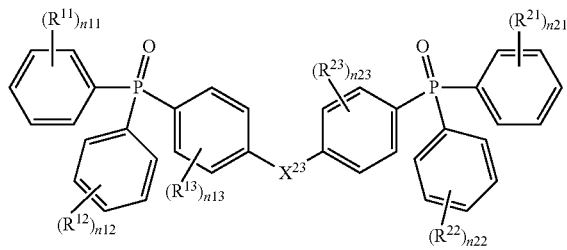

[In the general formula (2-3), $R^{11}$, $R^{12}$, $R^{13}$, $R^{21}$, $R^{22}$ and $R^{23}$ each independently represent a substituent, n11, n12, n21 and n22 each independently indicate an integer of from 0 to 5, n13 and n23 each independently indicate an integer of from 0 to 4, $X^{23}$ represents a linking group having any of the following structures.

[Chem. 15]

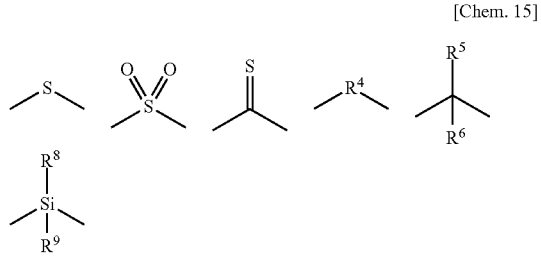

In the above-mentioned structures of the linking group, $R^4$ represents a substituted or unsubstituted aliphatic cyclic linking group. $R^5$ and $R^6$ each independently represent a hydrogen atom, a halogen atom, a substituted or unsubstituted alkyl group, or a substituted or unsubstituted aryl group. $R^7$, $R^8$ and $R^9$ each independently represent a hydrogen atom, a substituted or unsubstituted alkyl group, or a substituted or unsubstituted aryl group. At least one of $R^8$ and $R^9$ is a hydrogen atom, or a substituted or unsubstituted alkyl group.]

[6] The compound according to any one of [1] to [5], wherein the linking group has the following structure.

[Chem. 16]

[7] The compound according to any one of 1] to [5], wherein the linking group has any of the following structures.

[Chem. 17]

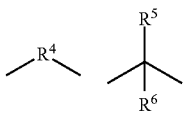

[8] The compound according to any one of [1] to [5], wherein the linking group has the following structure.

[Chem. 18]

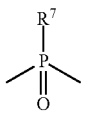

[9] The compound according to any one of [1] to [8], which has a lowest excited triplet energy level at 77° K of not lower than 2.80 eV.

[10] The compound according to any one of [1] to [8], which has a lowest excited triplet energy level at 77° K of not lower than 2.95 eV.

[11] A charge transport material comprising the compound of any one of [1] to [10].

[12] An organic device using the compound of any one of [1] to [10].

[13] An organic electroluminescence element using the compound of any one of [1] to [10].

Advantageous Effects of Invention

The compounds of the present invention have excellent physical properties as a charge transport material and are useful as an electronic device material. In addition, the organic electroluminescence element of the invention has a high luminescent efficiency.

DESCRIPTION OF EMBODIMENTS

Figure 1:
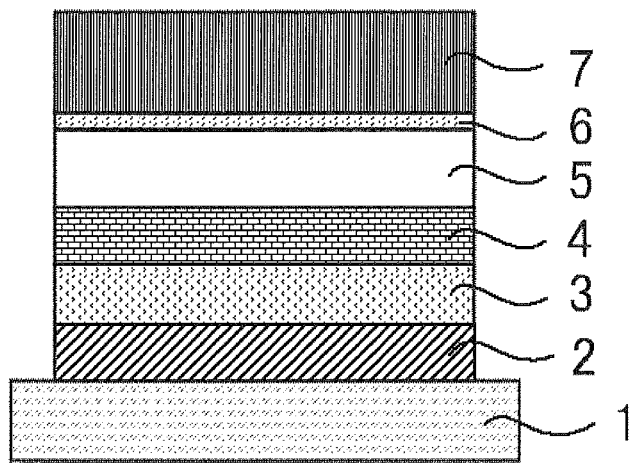
[FIG. 1] This is a schematic cross-sectional view showing a layer configuration of the organic electroluminescence element of Production Examples.

The contents of the invention are described in detail hereinunder. The description of the constitutive elements of the invention given hereinunder is for some typical embodiments and specific examples of the invention; however, the invention should not be limited to such embodiments and specific examples. In this description, the numerical range expressed by the wording "a number to another number" means the range that falls between the former number indicating the lower limit of the range and the latter number indicating the upper limit thereof.

[Compounds of the Invention]

The compounds of the invention are those having a structure represented by the following general formula (1):

General Formula (1)

[Chem. 19]

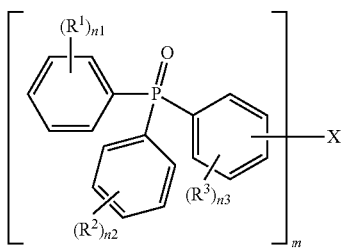

In the general formula (1), X represents a linking group having any of the structures mentioned below, m is equal to the valence of the linking group X and indicates an integer of from 2 to 4. $R^1$, $R^2$ and $R^3$ each independently represent a substituent, n1 and n2 each independently indicate an integer of from 0 to 5, n3 indicates an integer of from 0 to 4. When n1 is an integer of from 2 to 5, n1's $R^1$'s may be the same or different; when n2 is an integer of from 2 to 5, n2's $R^2$'s may be the same or different; when n3 is an integer of from 2 to 4, n3's $R^3$'s may be the same or different. Further, $R^1$, $R^2$, $R^3$, n1, n2 and n3 in m's structural units may be the same or different. $R^1$'s bonding to the adjacent carbon atoms of the benzene ring, $R^2$'s bonding to the adjacent carbon atoms of the benzene ring, and $R^3$'s bonding to the adjacent carbon atoms of the benzene ring may bond to each other to form a cyclic structure along with the adjacent carbon atoms of the benzene ring.

X in the general formula (1) is a linking group having any of the following structures. However, when X is —O— or —($R^7$) P(=O)—, this links at the 3,3'-positions of the triphenylphosphine oxide structure of the general formula (1). When X is >PO—, this links at the 3,3',3"-positions of the triphenylphosphine oxide structure.

[Chem. 20]

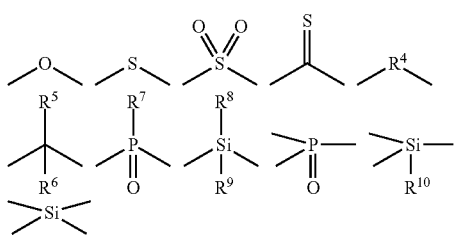

In the above-mentioned structures of the linking group, $R^4$ represents a substituted or unsubstituted aliphatic cyclic linking group. The aliphatic cyclic linking group comprises a cyclic skeleton of carbon atoms, and links to the group via the carbon atom constituting the cyclic skeleton. Preferably, the number of the carbon atoms constituting the cyclic skeleton is from 3 to 8, more preferably from 4 to 7, even more preferably 5 or 6, still more preferably 6. Specific examples of the aliphatic cyclic linking group includes a 1,1-cyclobutylene group, a 1,2-cyclobutylene group, a 1,1-cyclopentylene group, a 1,2-cyclopentylene group, a 1,3-cyclopentylene group, a 1,1-cyclohexylene group, a 1,2-cyclohexylene group, a 1,3-cyclohexylene group, a 1,1-cycloheptylene group, a 1,2-cycloheptylene group, a 1,3-cycloheptylene group, a 1,4-cycloheptylene group, a 1,1-cyclooctylene group, a 1,2-cyclooctylene group, a 1,3-cyclooctylene group, a 1,4-cyclooctylene group, a 2,2-adamantylene group, a 2,4-adamantylene group. Preferred specific examples of the aliphatic cyclic linking group include a 1,1-cyclopentylene group, a 1,2-cyclopentylene group, a 1,3-cyclopentylene group, a 1,1-cyclohexylene group, a 1,2-cyclohexylene group, a 1,3-cyclohexylene group, a 1,1-cycloheptylene group, a 1,2-cycloheptylene group, a 1,3-cycloheptylene group, a 2,2-adamantylene group, a 1,4-adamantylene group. More preferred specific examples of the aliphatic cyclic linking group include a 1,1-cyclopentylene-group, a 1,2-cyclopentylene group, a 1,3-cyclopentylene group, a 1,4-cyclohexylene group, a 2,2-adamantylene group, a 1,4-adamantylene group.

The aliphatic cyclic linking group that $R^4$ represents may be substituted. The substituent includes, for example, an alkyl group, an alkoxy group, an aryl group, an aryloxy group. For the description of these substituents and the preferred ranges thereof, referred to is the description of the corresponding groups given hereinunder.

In the above-mentioned structures of the linking group, $R^5$ and $R^6$ each independently represent a hydrogen atom, a halogen atom, a substituted or unsubstituted alkyl group, or a substituted or unsubstituted aryl group. $R^7$, $R^8$, $R^9$ and $R^{10}$ each independently represent a hydrogen atom, a substituted or unsubstituted alkyl group, or a substituted or unsubstituted aryl group, preferably a substituted or unsubstituted alkyl group or a substituted or unsubstituted aryl group.

The halogen atom which may be employed for $R^5$ and $R^6$ is preferably a fluorine atom, a chlorine atom, a bromine atom or an iodine atom, more preferably a fluorine atom or a chlorine atom, even more preferably a fluorine atom.

The alkyl group which may be employed for $R^5$, $R^6$, $R^7$, $R^8$, $R^9$ and $R^{10}$ may be linear or branched or cyclic. Preferred is a linear or branched alkyl group. The carbon number of the alkyl group is preferably from 1 to 20, more preferably 1 to 12, even more preferably from 1 to 6, still more preferably from 1 to 3 (or that is, a methyl group, an ethyl group, an n-propyl group, an isopropyl group). The cyclic alkyl group includes, for example, a cyclopentyl group, a cyclohexyl group, a cycloheptyl group.

The aryl group which may be employed for $R^5$, $R^6$, $R^7$, $R^8$, $R^9$ and $R^{10}$ may comprise one aromatic ring or may have a structure of two or more fused aromatic rings. The carbon number of the aryl group is preferably from 6 to 22, more preferably from 6 to 18, even more preferably from 6 to 14, still more preferably from 6 to 10 (or that is, a phenyl group, a 1-naphthyl group, a 2-naphthyl group).

The above-mentioned alkyl group may be further substituted or may not be substituted. The substituent in the substituted case includes, for example, an alkoxy group, an aryl group and an aryloxy group. For the description and the preferred range of the aryl group as the substituent, referred to is the description of the aryl group given hereinabove.

The aryl group may be further substituted or may not be substituted. The substituent in the substituted case includes, for example, an alkyl group, an alkoxy group, an aryl group and an aryloxy group. For the description and the preferred ranges of the aryl group and the aryl group, referred to is the description of the alkyl group and the aryl group given hereinabove.

The alkoxy group which may be employed as the substituent may be linear or branched or cyclic. Preferred is a linear or branched alkoxy group. The carbon number of the alkoxy group is preferably from 1 to 20, more preferably from 1 to 12, even more preferably from 1 to 6, still more preferably from 1 to 3 (or that is, a methoxy group, an ethoxy group, an n-propoxy group, an isopropoxy group). The cyclic alkoxy group includes, for example, a cyclopentyloxy group, a cyclohexyloxy group, a cycloheptyloxy group.

The aryloxy group which may be employed as the substituent may comprise one aromatic ring or may have a structure of two or more fused aromatic rings. The carbon number of the aryloxy group is preferably from 6 to 22, more preferably from 6 to 18, even more preferably from 6 to 14, still more preferably from 6 to 10 (or that is, a phenyloxy group, a 1-naphthyloxy group, a 2-naphthyloxy group).

At least one of $R^8$ and $R^9$ is a hydrogen atom, or a substituted or unsubstituted alkyl group.

Of the structures of the linking group having $R^4$, $R^5$, $R^6$, $R^7$, $R^8$, $R^9$ or $R^{10}$ mentioned above, preferred examples are shown below.

[Chem. 21]

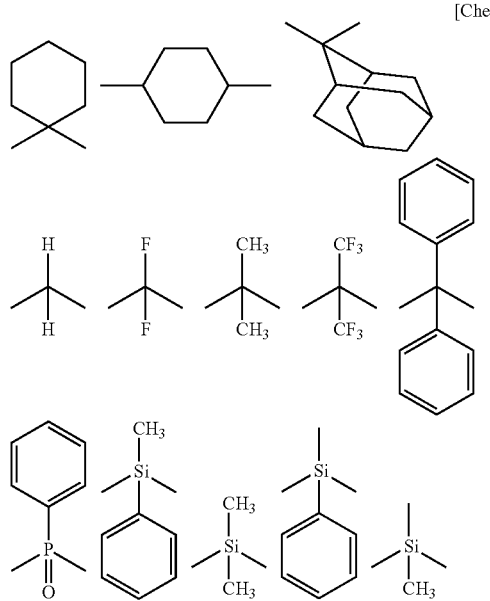

As X in the general formula (1), for example, the following linking groups may be summarized in a group.

[Chem. 22]

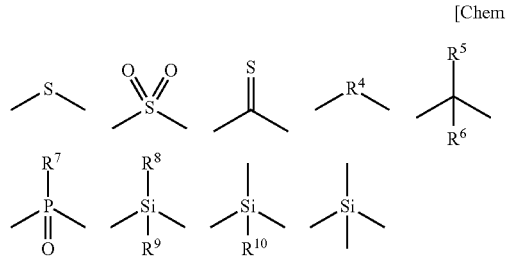

As X in the general formula (1), for example, the following linking groups may also be summarized in a group.

[Chem. 23]

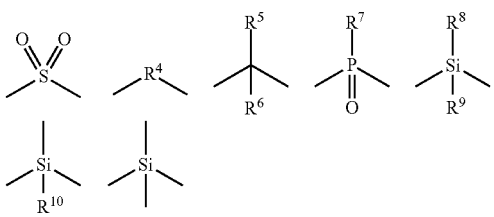

X in the general formula (1) is preferably a divalent linking group, and m is preferably 2.

The substituent that $R^1$, $R^2$ and $R^3$ in the general formula (1) each represent includes, for example, a substituted or unsubstituted alkyl group, a substituted or unsubstituted alkoxy group, a substituted or unsubstituted aryl group, a substituted or unsubstituted aryloxy group, a substituted or unsubstituted alkenyl group, a substituted or unsubstituted amino group, a halogen atom, and a cyano group. Preferably, the substituent is a substituted or unsubstituted alkyl group, a substituted or unsubstituted aryl group, a substituted or unsubstituted alkoxy group or a substituted or unsubstituted aryloxy group, and more preferably a substituted or unsubstituted alkyl group or a substituted or unsubstituted aryl group.

The description and the preferred ranges of the alkyl group, the alkoxy group, the aryl group and the aryloxy group that may be employed as the substituent are the same as the description and the preferred ranges of the alkyl group and the aryl group that the above-mentioned $R^5$, $R^6$, $R^7$, $R^8$, $R^9$ and $R^{10}$ each represent, and the description and the preferred ranges of the alkoxy group and the aryloxy group which may be employed as the above-mentioned substituent.

The alkenyl group which may be employed as the substituent may be linear, branched or cyclic. Preferred is a linear or branched alkenyl group. The carbon number of the alkenyl group is preferably from 2 to 20, more preferably from 2 to 12, even more preferably from 2 to 6, still more preferably 2 or 3 (or that is, a vinyl group, a 1-propenyl group, a 2-propenyl group). The cyclic alkenyl group includes, for example, a cyclopentenyl group, a cyclohexenyl group and a cycloheptenyl group. The alkenyl group may be further substituted, and the substituent in the substituted case includes an alkyl group, an aryl group, an alkoxy group, an aryloxy group, etc. The description and the preferred ranges of these substituents are the same as the description and the preferred ranges of the alkyl group and the aryl group that the above-mentioned $R^5$, $R^6$, $R^7$, $R^8$, $R^9$ and $R^{10}$ each represent, and the description and the preferred ranges of the alkoxy group and the aryloxy group which may be employed as the above-mentioned substituent.

The amino group which may be employed as the substituent includes an unsubstituted amino group and a substituted amino group. The substituent of the substituted amino group includes an alkyl group and an aryl group. The description and the preferred ranges of these substituents are the same as the description and the preferred ranges of the alkyl group and the aryl group that the above-mentioned $R^5$, $R^6$, $R^7$, $R^8$, $R^9$ and $R^{10}$ each represent.

The halogen atom which may be employed as the substituent includes, for example, a fluorine atom, a chlorine atom, a bromine atom, an iodine atom. Preferred are a fluorine atom, a chlorine atom and a bromine atom; more preferred are a fluorine atom and a chlorine atom; and even more preferred is a fluorine atom.

As the substituent that $R^1$, $R^2$ and $R^3$ in the general formula (1) each represent, also mentioned here is the substituent represented by the following general formula (11).

General Formula (11)

[Chem. 24]

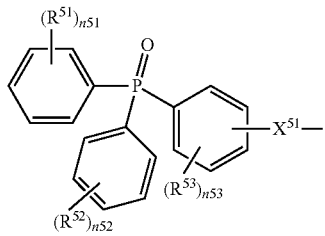

In the general formula (11), $X^{51}$ represents a divalent linking group having any of the structures to be mentioned below. $R^{51}$, $R^{52}$ and $R^{53}$ each independently represent a substituent; n51 and n52 each independently indicate an integer of from 0 to 5; n53 indicates an integer of from 0 to 4. When n51 is an integer of from 2 to 5, n51's $R^{51}$'s may be the same or different; when n52 is an integer of from 2 to 5, n52's $R^{52}$'s may be the same or different; and when n53 is an integer of from 2 to 4, n53's $R^{53}$'s may be the same or different. $R^{51}$'s bonding to the adjacent carbon atoms of the benzene ring, $R^{52}$'s bonding to the adjacent carbon atoms of the benzene ring, and $R^{53}$'s bonding to the adjacent carbon atoms of the benzene ring may bond to each other to form a cyclic structure along with the adjacent carbon atoms of the benzene ring. Specific examples and the preferred ranges of the substituents of $R^{51}$, $R^{52}$ and $R^{53}$ in the general formula (11) are the same as the specific examples and the preferred ranges of the substituents of $R^1$, $R^2$ and $R^3$ in the general formula (1).

$X^{51}$ in the general formula (11) is a linking group having any of the following structures. The description and the preferred ranges of $R^4$, $R^5$, $R^6$, $R^7$, $R^8$ and $R^9$ are the same as in the general formula (1). In the compounds of the invention, $X^{51}$ may be the same as or different from X, but preferably the two are the same.

[Chem. 25]

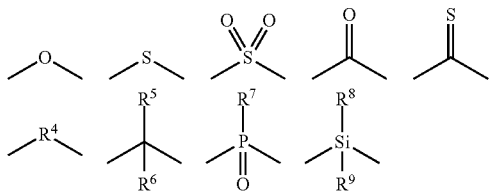

The substituents represented by $R^1$, $R^2$ and $R^3$ in the general formula (1) may be the same or different. When the molecule has multiple $R^1$'s, those multiple $R^1$'s may be the same or different. The same shall apply to the other cases where the molecule has multiple $R^2$'s and where the molecule has multiple $R^3$'s.

Preferably, n1, n2 and n3 in the general formula (1) each are independently an integer of from 0 to 3, more preferably an integer of from 0 to 2. Also preferably, n1 and n2 and n3 are all 0.

Of the compounds represented by the general formula (1), preferred here is use of the compounds represented by the following general formula (2).

General Formula (2)

[Chem. 26]

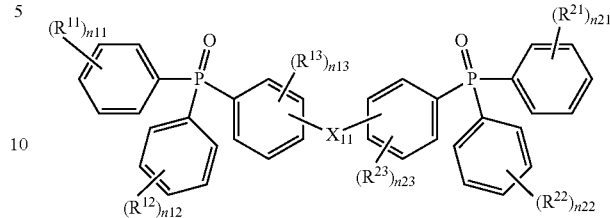

In the general formula (2), $X^{11}$ represents a divalent linking group having any of the structures mentioned below. $R^{11}$, $R^{12}$, $R^{13}$, $R^{21}$, $R^{22}$ and $R^{23}$ each independently represent a substituent, n11, n12, n21 and n22 each independently indicate an integer of from 0 to 5, n13 and n23 each independently indicate an integer of from 0 to 4. When n11 is an integer of from 2 to 5, n11's $R^{11}$'s may be the same or different; when n12 is an integer of from 2 to 5, n12's $R^{12}$'s may be the same or different; when n13 is an integer of from 2 to 4, n13's $R^{13}$'s may be the same or different; when n21 is an integer of from 2 to 5, n21's $R^{21}$'s may be the same or different; when n22 is an integer of from 2 to 5, n22's $R^{22}$'s may be the same or different; when n23 is an integer of from 2 to 4, n23's $R^{23}$'s may be the same or different. Specific examples and preferred ranges of the substituents of $R^{11}$, $R^{12}$, $R^{13}$, $R^{21}$, $R^{22}$ and $R^{23}$ in the general formula (2) are the same as the specific examples and the preferred ranges of the substituents of $R^1$, $R^2$ and $R^3$ in the general formula (1).

$X^{11}$ in the general formula (2) is a linking group having any of the following structures. The description and the preferred examples of $R^4$, $R^5$, $R^6$, $R^7$, $R^8$ and $R^9$ are the same as those in the general formula (1). When X is —O— or —($R^7$)P(=O)—, this links at the 3,3'-positions of the triphenylphosphine oxide structure of the general formula (2).

[Chem. 27]

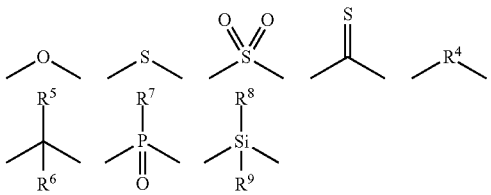

As $X^{11}$ in the general formula (2), for example, the following linking groups may be summarized in a group.

[Chem. 28]

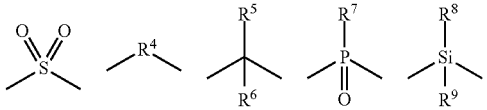

The general formula (2) includes the following general formula (2-1), general formula (2-2) and general formula (2-3). Of those, more preferred are the compounds represented by the general formula (2-1) and the compounds represented by the general formula (2-3). The compounds represented by the general formula (2-1) are preferred since they hardly crystallize; and the compounds represented by the general formula (2-3) are preferred since the lowest excited triplet energy level thereof is high.

General Formula (2-1)

[Chem. 29]

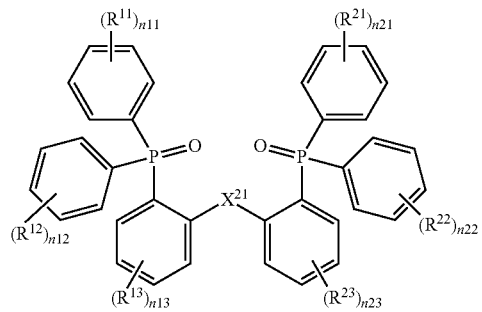

The description, the specific examples and the preferred ranges of $R^{11}, R^{12}, R^{13}, R^{21}, R^{22}, R^{23}$, n11, n12, n13, n21, n22 and n23 in the general formula (2-1) are the same as in the formula (2). $X^{21}$ in the general formula (2-1) represents a linking group having any of the following structures. The description and the preferred ranges of $R^4, R^5, R^6, R^7, R^8$ and $R^9$ are the same as in the general formula (1).

[Chem. 30]

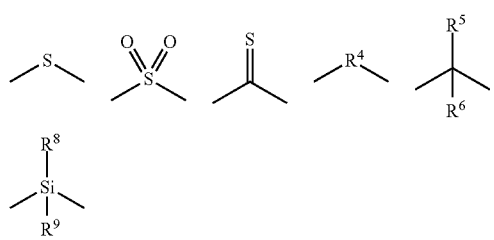

As $X^{21}$ in the general formula (2-1), for example, the following linking groups may be summarized in a group.

[Chem. 31]

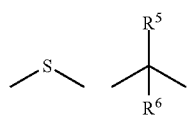

Of those, preferred are the following linking groups.

[Chem. 32]

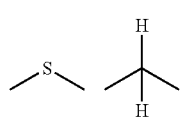

General Formula (2-2)

-continued

[Chem. 33]

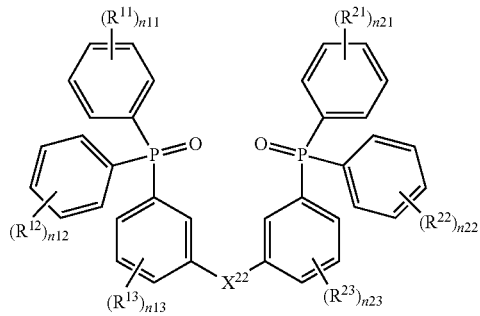

The description, the specific examples and the preferred ranges of $R^{11}, R^{12}, R^{13}, R^{21}, R^{22}, R^{23}$, n11, n12, n13, n21, n22 and n23 in the general formula (2-2) are the same as in the formula (2). $X^{22}$ in the general formula (2-2) represents a linking group having any of the following structures. The description and the preferred ranges of $R^4, R^5, R^6, R^7, R^8$ and $R^9$ are the same as in the general formula (1).

[Chem. 34]

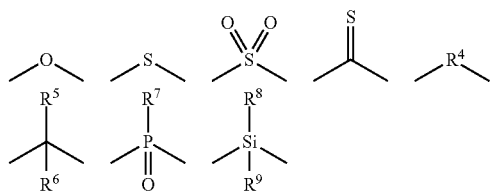

As $X^{22}$ in the general formula (2-2), for example, the following linking groups may be summarized in a group.

[Chem. 35]

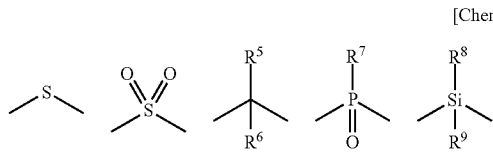

Of those, preferred are the following linking groups.

[Chem. 36]

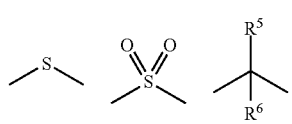

General Formula (2-3)

[Chem. 37]

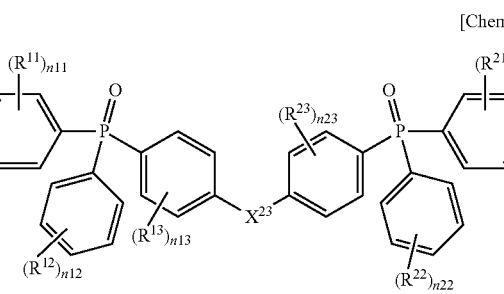

The description, the specific examples and the preferred ranges of $R^{11}, R^{12}, R^{13}, R^{21}, R^{22}, R^{23}$, n11, n12, n13, n21, n22 and n23 in the general formula (2-3) are the same as in the formula (2). $X^{23}$ in the general formula (2-3) represents a linking group having any of the following structures. The description and the preferred ranges of $R^4$, $R^5$, $R^6$, $R^7$, $R^8$ and $R^9$ are the same as in the general formula (1).

[Chem. 38]

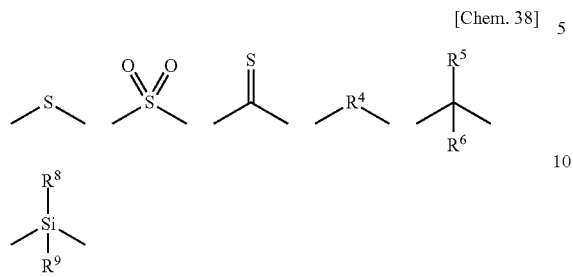

As $X^{23}$ in the general formula (2-3), for example, the following linking groups may be summarized in a group.

[Chem. 39]

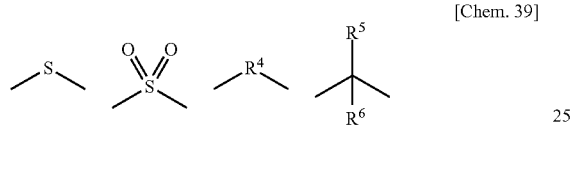

Specific examples of the compounds represented by the general formula (1) are shown below; however, the compounds represented by the general formula (1) for use in the invention are not limitatively interpreted by those specific examples. In the structural formulae of the following specific examples, Ph means a phenyl group.

[Chem. 40]

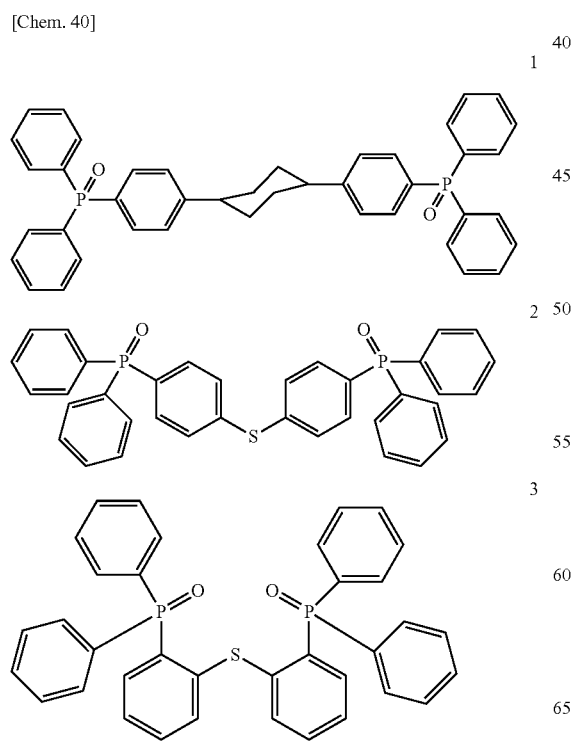

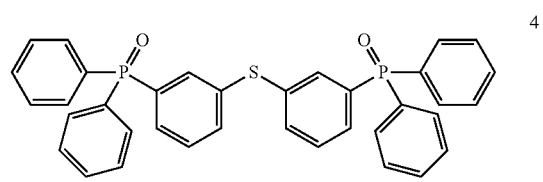

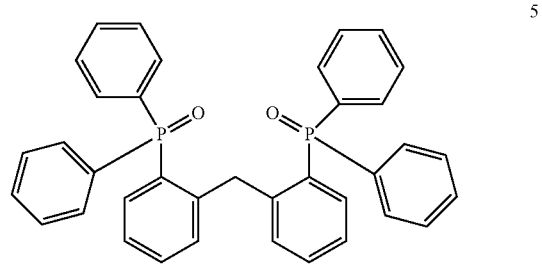

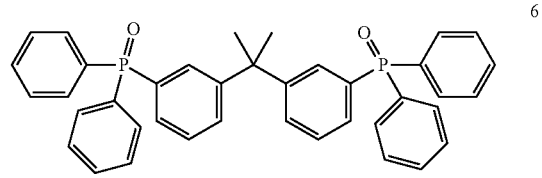

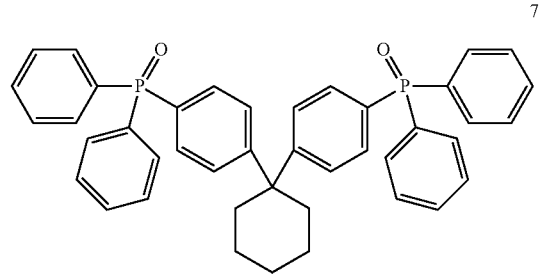

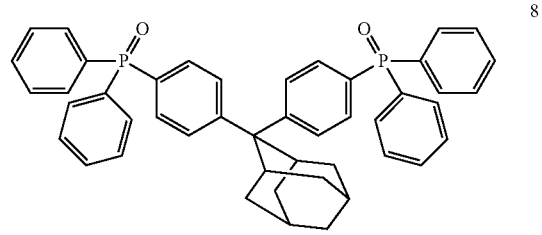

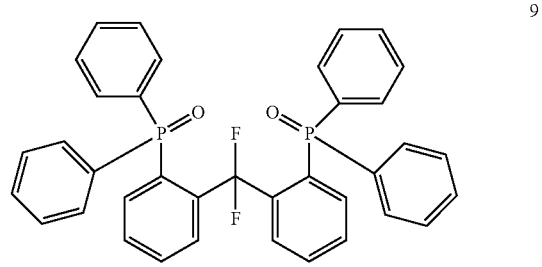

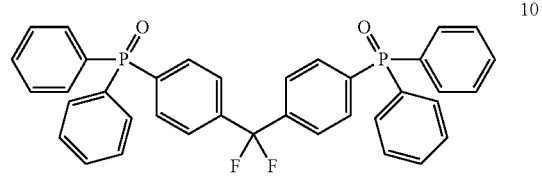

-continued

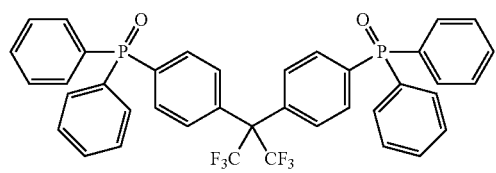
11

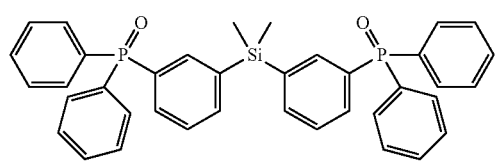
12

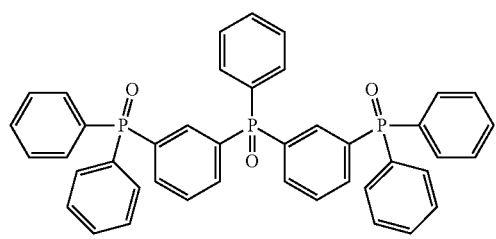
13

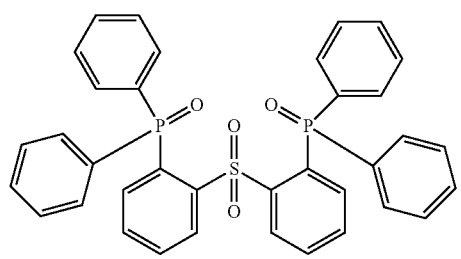
14

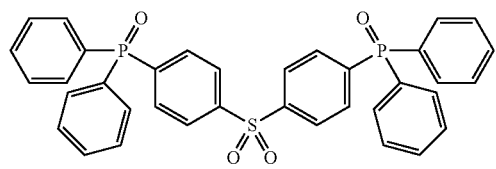
15

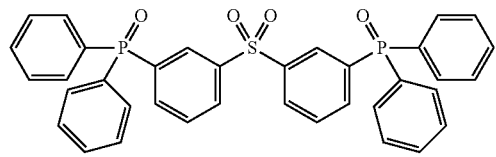
16

[Chem. 41]

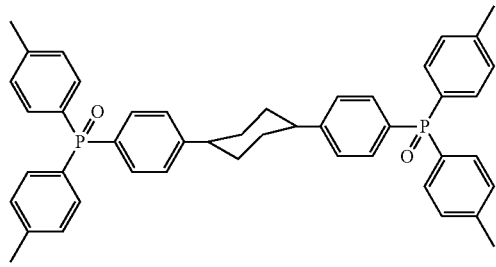
17

-continued

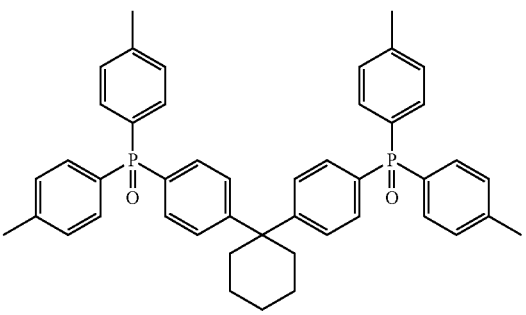
18

[Production Method for Compounds of the Invention]

The production method for the compounds represented by the general formula (1) is not specifically defined. The compounds represented by the general formula (1) may be produced by suitably combining known production methods and conditions.

For example, one preferred production method is represented by the following scheme 1. Briefly, the production method comprises converting a triphenylphosphine dimer to tetramer represented by the general formula (21) into the corresponding triphenylphosphine oxide dimer to tetramer represented by the general formula (1). For the conversion, preferably used is hydrogen peroxide. For the reaction condition, referred to is the known reaction condition that is employed in converting triphenylphosphine into triphenylphosphine oxide.

Scheme 1:

[Chem. 42]

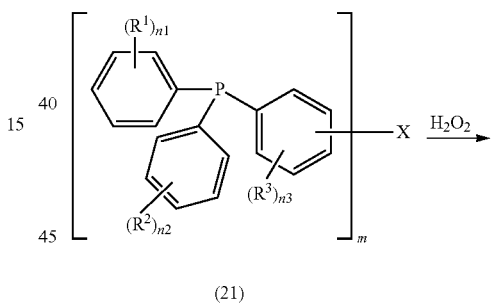

(21)

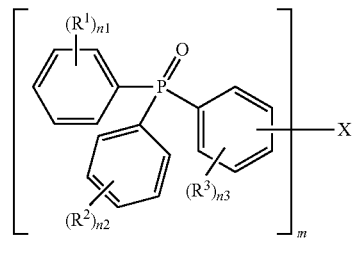

(1)

The compound represented by the general formula (21) may be produced by suitably selecting and combining known production methods. For example, according to the following scheme 2, a diphenylphosphine derivative represented by the general formula (22) is coupled with a phenyl dimer to tetramer represented by the general formula (23) to give the corresponding compound represented by the general formula (21). $Z^1$ in the general formula (22) and $Z^2$ in the general formula (23) are so selected as to be a combination capable of efficiently attaining the coupling reaction. For example, it is desirable that Na is selected as $Z^1$ and a halogen atom such as a fluorine atom or the like is selected as $Z^2$.

Scheme 2

[Chem. 43]

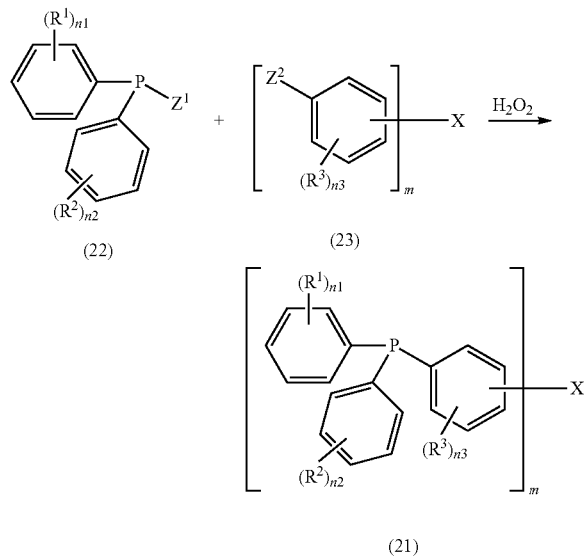

[Physical Properties of Compounds of the Invention]

The compounds represented by the general formula (1) have a relatively high lowest excited triplet energy level at 77° K and have excellent properties as a charge transport material, and therefore can be effectively used in electronic devices such as organic electroluminescence elements, etc. The lowest excited triplet energy level at 77° K is preferably not lower than 2.80 eV, more preferably not lower than 2.85 eV, even more preferably not lower than 2.90 eV, still more preferably not lower than 3.00 eV, further more preferably not lower than 3.03 eV. The lowest excited triplet energy level as referred to in the invention is a value determined by measuring the PL spectrum at 77° K of a thin film of the compound formed on a quartz substrate followed by calculating the energy at the peak value on the shortest wavelength side. Accordingly, the value of the lowest excited triplet energy level in the invention differs from the numerical value measured in a solution state of the compound. For providing a material having a high lowest excited triplet energy level in a thin film state, it is important to prevent association by intermolecular hydrogen bonding, and for this, the present inventors have found that the structure of represented by the general formula (1) is advantageous.

The type of the devices that favorably use the compounds represented by the general formula (1) is not specifically defined, but for example, there are mentioned organic electroluminescence elements and electrophotographic photoreceptors. In addition, the compounds can be effectively used also for photoelectric conversion elements, and therefore can be effectively used also for organic thin-film solar cells. Further, the compounds can be effectively used for organic transistors. As a typical device, hereinafter described is an organic electroluminescence element.

[Organic Electroluminescence Element]

A typical organic electroluminescence element is so configured that an anode of ITO or the like, an organic layer and a cathode are laminated on a transparent substrate of glass or the like. The organic layer generally has a structure of laminated multiple layers each containing an organic compound, and depending on the functions thereof, the constitutive layers are referred to as a hole injection layer, a hole transport layer, a light-emitting layer, an electron transport layer, an electron injection layer, etc. In this description, as a general configuration example of the organic electroluminescence element, described is a case of an organic electroluminescence element that comprises, as laminated in that order, an anode, a first organic layer mainly composed of a first organic material, a second organic layer mainly composed of a second organic material and a cathode.

The first organic layer is a layer that mainly fulfills a hole transport function, and when the first organic layer is doped with a light-emitting material, the first organic layer additionally fulfills a function of transporting electrons to the light-emitting material. The first organic layer is mainly formed of such a first organic material that fulfills the function, and "mainly" as referred to herein is meant to indicate the organic material of which the content is the largest of all the organic materials constituting the first organic layer. In general, the content is at least 50% by weight, preferably at least 60% by weight, more preferably at least 70% by weight.

The second organic layer is a layer mainly fulfilling an electron transport function, and when the second organic layer is doped with a light-emitting material, the second organic layer additionally fulfills a function of transporting holes to the light-emitting material. The second organic layer is mainly formed of such a second organic material that fulfills the function, and "mainly" as referred to herein is meant to indicate the organic material of which the content is the largest of all the organic materials constituting the second organic layer. In general, the content is at least 50% by weight, preferably at least 60% by weight, more preferably at least 70% by weight.

Any other layer may be laminated between the anode and the first organic layer constituting the organic electroluminescence element. For example, an organic layer having a hole injection function, an organic layer having a hole transport function, and an organic layer having an electron blocking function may be laminated.

In addition, any other layer may also be laminated between the cathode and the second organic layer constituting the organic electroluminescence element. For example, an organic layer having an electron injection function, an organic layer having an electron transport function, and an organic layer having a hole blocking function may be laminated.

In the organic electroluminescence element, a light-emitting material is contained in at least any one of the first organic layer or the second organic layer. Accordingly, a light-emitting material may be contained only in the first organic layer or only in the second organic layer, or may be contained both in the first organic layer and in the second organic layer. Preferred is an embodiment where a light-emitting material is contained only in the first organic layer, or only in the second organic layer, and more preferred is an embodiment where the material is contained only in the first organic layer.

In case where a light-emitting material is contained only in the first organic layer of the organic electroluminescence element, preferably, the thickness of the second organic layer is at least 40 nm, more preferably at least 50 nm. On the other hand, in case where a light-emitting material is contained only in the second organic layer of the organic electroluminescence element, preferably, the thickness of the first organic layer is at least 30 nm, more preferably at least 50 nm. Employing the embodiment prevents quenching of exciton generated in the organic layer to which a light-emitting material has been added, therefore greatly enlarging the luminescent efficiency.

The content of the light-emitting material is preferably at least 0.1% by weight of the organic layer that contains the light-emitting material, more preferably at least 1.0% by weight, even more preferably at least 3.0% by weight. Also preferably, the content of the light-emitting material is at most 30% by weight of the organic layer that contains the light-emitting material, more preferably at most 20% by weight, even more preferably at most 10% by weight.

Preferably, the organic electroluminescence element satisfies the following formula (A) and formula (B).

$T1(\text{first}) - T1(\text{light emission}) > 0.19 \text{ eV}$   Formula (A)

$T1(\text{second}) - T1(\text{light emission}) > 0.24 \text{ eV}$   Formula (B)

In the above formulae, T1 (first) means the lowest excited triplet energy level at 77° K of the first organic material; T1 (second) means the lowest excited triplet energy level at 77° K of the second organic material; and T1 (emission) means the lowest excited triplet energy level at 77° K of the light-emitting material.

In conventional studies, the relationship between the lowest excited triplet energy level of a light-emitting material and the lowest excited triplet energy level of an organic material that constitutes an organic layer to which the light-emitting material has been added has become specifically noted. Regarding this, the present inventors have found for the first time that the lowest excited triplet energy level of a thin film of the organic material that constitutes the organic layer adjacent to the layer to which the light-emitting material has been added must also be taken into consideration. With that, the inventors have further found that the existence of an energy difference on a certain level or more between the lowest excited triplet energy level of a thin film of the organic material that constituted the adjacent organic layer and the lowest excited triplet energy level of a thin film of the light-emitting material is also an important matter for increasing the luminescent efficiency of an organic electroluminescence element. On the basis of those findings, the present inventors have developed the above-mentioned formula (A) and formula (B).

Preferably, the organic electroluminescence element of the invention further satisfies the following formula (A-1), more preferably the following formula (A-2), and even more preferably the following formula (A-3).

$T1(\text{first}) - T1(\text{light emission}) > 0.21 \text{ eV}$   Formula (A-1)

$T1(\text{first}) - T1(\text{light emission}) > 0.23 \text{ eV}$   Formula (A-2)

$T1(\text{first}) - T1(\text{light emission}) > 0.25 \text{ eV}$   Formula (A-3)

Also preferably, the organic electroluminescence element of the invention further satisfies the following formula (B-1), more preferably the following formula (B-2), and even more preferably the following formula (B-3).

$T1(\text{second}) - T1(\text{light emission}) > 0.29 \text{ eV}$   Formula (B-1)

$T1(\text{second}) - T1(\text{light emission}) > 0.34 \text{ eV}$   Formula (B-2)

$T1(\text{second}) - T1(\text{light emission}) > 0.40 \text{ eV}$   Formula (B-3)

Preferably, in the organic electroluminescence element of the invention, the lowest excited triplet energy level at 77° K of the first organic material [T1 (first)] is at least 2.80 eV, more preferably at least 2.85 eV, even more preferably at least 2.90 eV, still more preferably at least 2.92 eV. Also preferably, the lowest excited triplet energy level at 77° K of the second organic material [T1 (second)] is at least 2.80 eV, more preferably at least 2.95 eV, even more preferably at least 3.00 eV, still more preferably at least 3.03 eV, further more preferably at least 3.05 eV. Preferably, the lowest excited triplet energy level at 77° K of the organic material [T1 (first)] is from 2.0 to 2.8 eV, more preferably from 2.4 to 2.8 eV, even more preferably from 2.6 to 2.8 eV.

The organic electroluminescence element of the invention that satisfies the formula (A) and the formula (B) is characterized in that the luminescent efficiency thereof is extremely high. As concretely shown in Examples given hereinunder, a case using FIrpic as the light-emitting material attained an external quantum efficiency of 18%; and a case using a Cu complex as the light-emitting material also attained an external quantum efficiency of more than 15%.

For example, in the conventional organic electroluminescence elements described in NPL 2 and NPL 4, the lowest excited triplet energy level at 77° K of the light-emitting material FIrpic is 2.67 eV, while in the hole transport layer adjacent to the light-emitting layer doped with the light-emitting material, merely used is 4,4',4"-tris(carbazol-9-yl)triphenylamine (TCTA) having a lowest excited triplet energy level at 77° K of 2.70 eV. T1 (first)–T1 (emission) is 0.06 eV and is small, and therefore the luminescent efficiency of the conventional elements could not be so high as that of the organic electroluminescence element satisfying the formula (A) and the formula (B) of the invention.

The compound represented by the general formula (1) can be used as the first organic material in the organic electroluminescence element or can also be used as the second organic material therein, or can be used as both the first organic material and the second organic material therein. Preferably, the compound is used as only the first organic material or as only the second organic material. In case where the compound represented by the general formula (1) is used as the second organic material, preferably, the light-emitting material is contained in the first organic material but may be contained in the second organic material.

Compounds except those of the general formula (1) that may be used as the second organic material in the invention are shown below. The second organic material for use in the invention should not be limitatively interpreted by these exemplifications.

[Chem. 44]

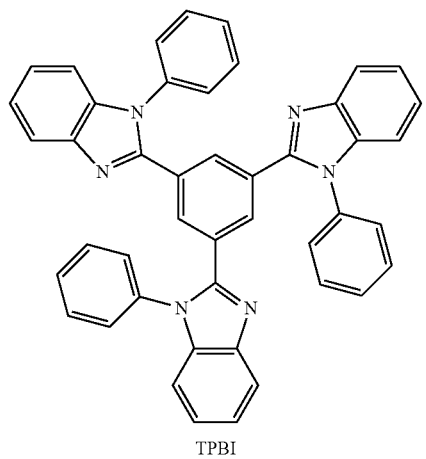

TPBI

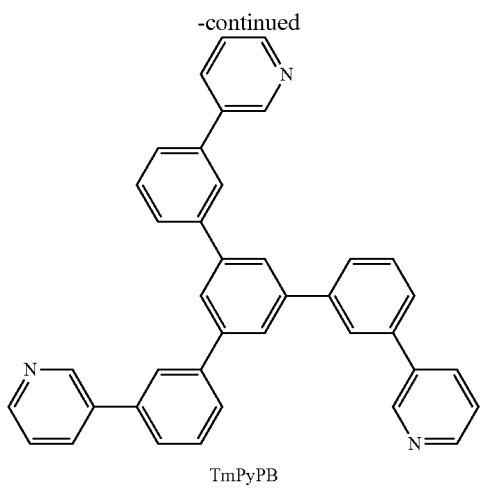

TmPyPB

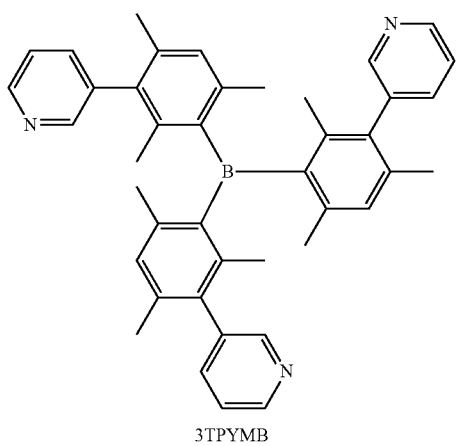

3TPYMB

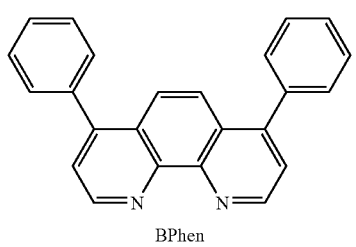

BPhen

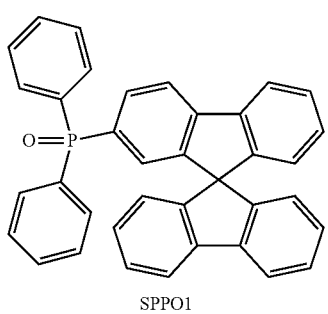

SPPO1

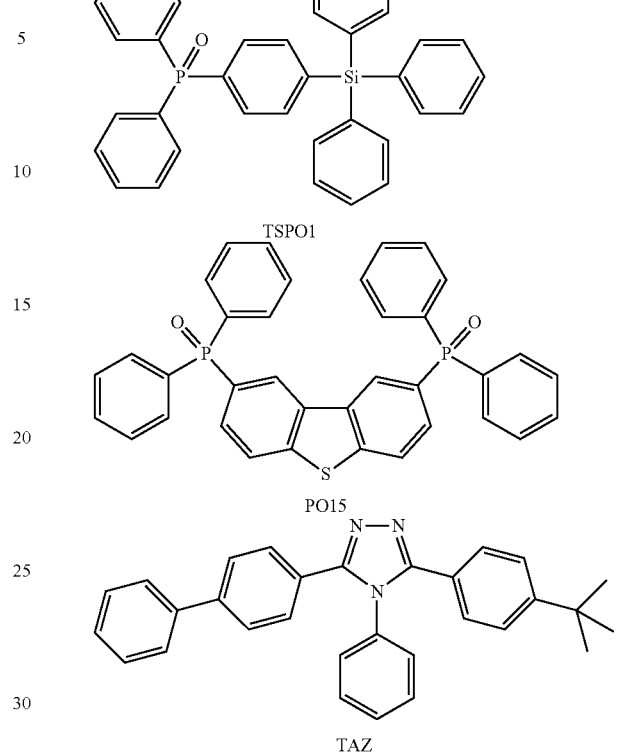

TSPO1

PO15

TAZ

As the first organic material for use in the organic electroluminescence element of the invention, for example, compounds represented by the following general formula (4) are preferably used.

General Formula (4)

[Chem. 45]

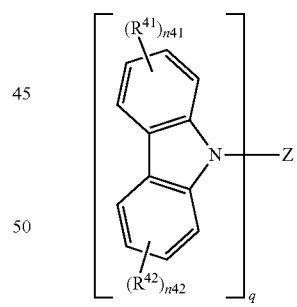

In the general formula (4) Z represents a q-valent linking group, and q indicates an integer of from 2 to 4. $R^{41}$ and $R^{42}$ each independently represent a substituent, and n41 and n42 each independently indicate an integer of from 0 to 4. When n41 is an integer of from 2 to 4, n41's $R^{41}$'s may be the same or different, and when n42 is an integer of from 2 to 4, n42's $R^{42}$'s may be the same or different. In addition, q's $R^{41}$, $R^{42}$, n41 and n42 each may be the same or different.

Z in the general formula (4) is preferably a linking group containing an aromatic ring or a hetero ring. The aromatic ring may be a single ring or may be a fused ring of two or more aromatic rings fused together. Preferably, the carbon number of the aromatic ring is from 6 to 22, more preferably from 6 to 18, even more preferably from 6 to 14, still more preferably from 6 to 10. Specific examples of the aromatic ring include a benzene ring and a naphthalene ring. The hetero ring may be a single ring or may also be a fused ring composed of one or more hetero rings fused with an aromatic ring or a hetero ring. Preferably, the carbon number of the hetero ring is from 5 to 22, more preferably from 5 to 18, even more preferably from 5 to 14, still more preferably from 5 to 10. Preferably, the hetero atom constituting the hetero ring is a nitrogen atom. Specific examples of the hetero ring include a pyridine ring, a pyridazine ring, a pyrimidine ring, a triazine ring, a triazole ring, a benzotriazole ring. Z in the general formula (4) may contain a nonaromatic linking group along with an aromatic ring or a hetero ring. The nonaromatic linking group includes those having any of the following structures.

[Chem. 46]

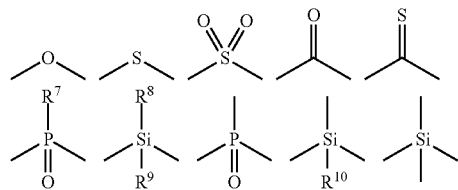

For the description and the preferred ranges of $R^7$, $R^8$, $R^9$ and $R^{10}$ in the above-mentioned nonaromatic linking group, referred to are the description and the preferred ranges of X in the above-mentioned general formula (1).

For the description and the preferred ranges of the substituents $R^{41}$ and $R^{42}$ in the general formula (4), referred to are the description and the preferred ranges of $R^1$ and $R^2$ in the above-mentioned general formula (1). Further, for the description and the preferred ranges of n41 and n42 in the general formula (4), referred to are the description and the preferred ranges of n3 in the above-mentioned general formula (1).

As the first organic material for use in the organic electroluminescence element of the invention, also preferably used are the compounds represented by the following general formula (5).

General Formula (5)

[Chem. 47]

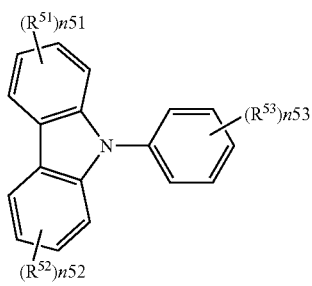

In the general formula (5), $R^{51}$, $R^{52}$ and $R^{53}$ each independently represent a substituent, n51 and n52 each independently indicate an integer of from 1 to 4, and n53 indicates an integer of from 1 to 5. At least one $R^{51}$, at least one $R^{52}$, and at least one $R^{53}$ each are an aryl group. When n51 is an integer of from 2 to 4, n51's $R^{51}$'s may be the same or different. When n52 is an integer of from 2 to 4, n52's $R^{52}$'s may be the same or different. When n53 is an integer of from 2 to 5, n53's $R^{53}$'s may be the same or different.

For the description and the preferred ranges of the substituents $R^{51}$, $R^{52}$ and $R^{53}$ and the aryl group in the general formula (5), referred to are the description and the preferred ranges of $R^1$, $R^2$ and $R^3$ of the above-mentioned general formula (1). Further, in the general formula (5), n51, n52 and n53 each are preferably from 1 to 3, more preferably 1 or 2.

Specific examples of the compounds represented by the general formula (4) or the general formula (5) are shown below. However, the compounds represented by the general formula (4) or the general formula (5) for use in the invention should not be limitatively interpreted by these exemplifications.

[Chem. 48]

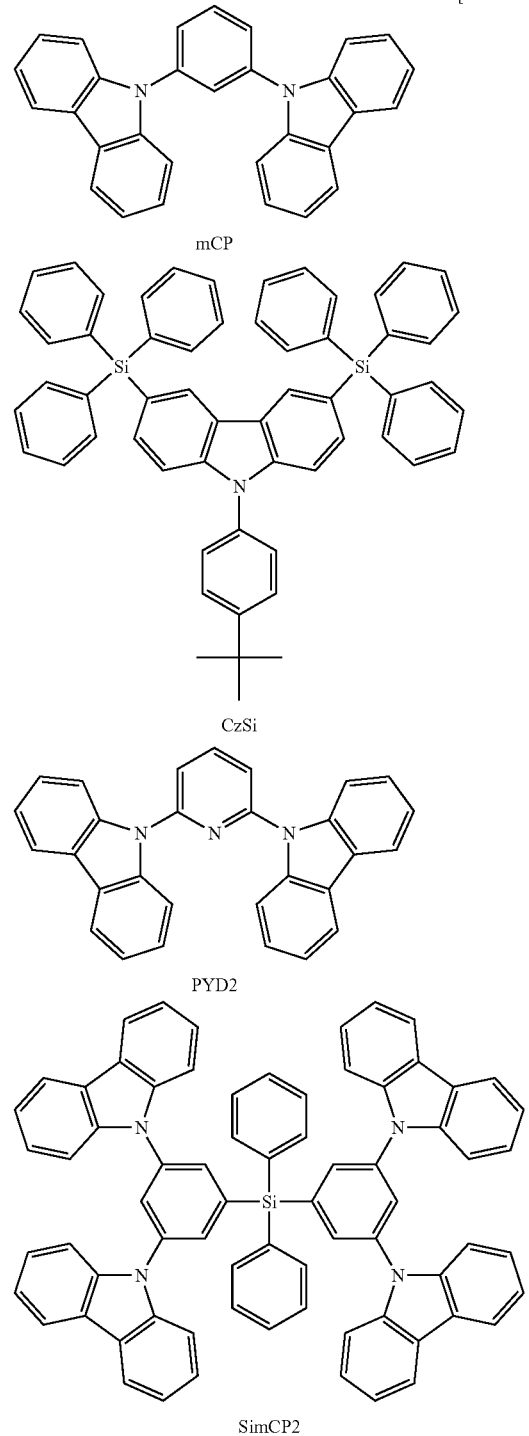

-continued

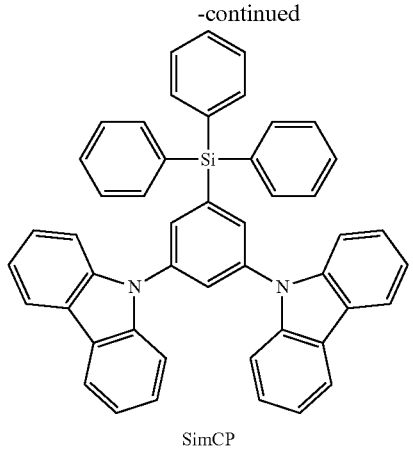
SimCP

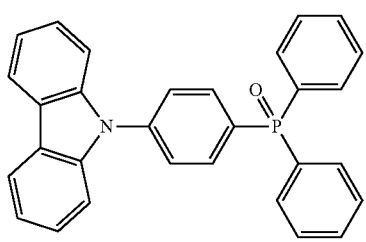
PO12

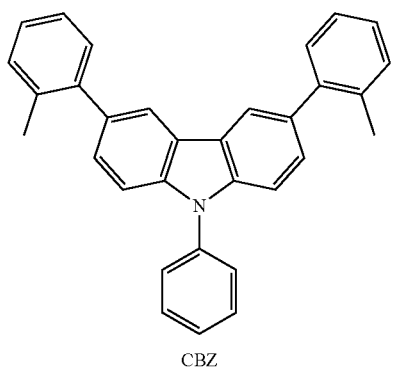
CBZ

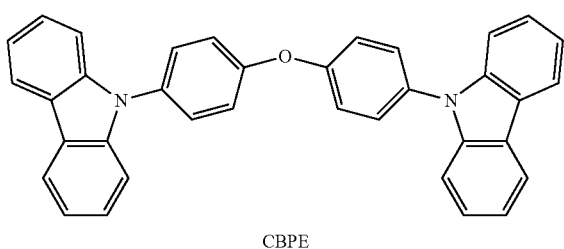
CBPE

The compounds usable as the first organic material in the invention are not limited to those represented by the general formula (4) or the general formula (5), and for example, other organic compounds generally usable in organic electroluminescence elements such as typically those mentioned below are also usable here.

[Chem. 49]

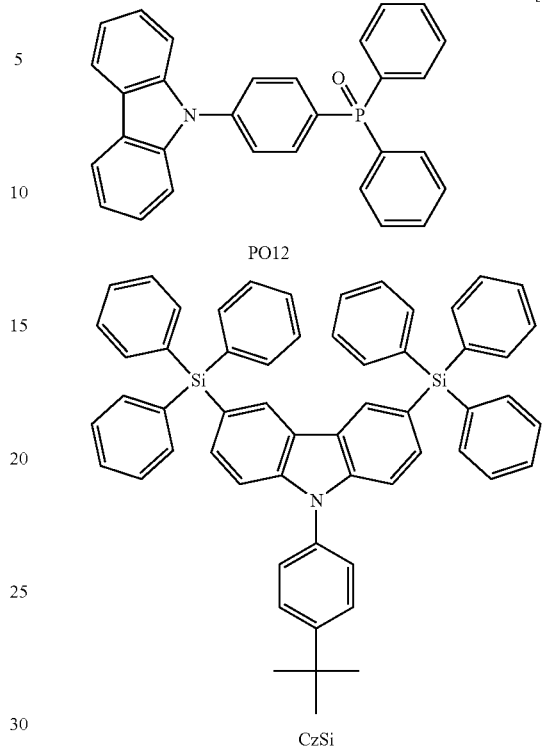

PO12

CzSi

The light-emitting material for use in the organic electroluminescence element of the invention may be selected in consideration of the wavelength at which the material is desired to emit light, etc. For example, phosphorescent materials, thermal activation-type delayed fluorescent materials, exciplex-type light-emitting materials, etc.

The phosphorescent materials include various known conventional metal complexes. In the invention, materials capable of emitting deep blue phosphorescent glow are preferably selected. Preferred examples of the phosphorescent materials include Ir complexes such as FIrpic, FCNIr, Ir(dbfmi), FIr6, Ir(fbppz)$_2$(dfbdp), FIrN4, etc.; Cu complexes such as [Cu(dnbp)(DPEPhos)]BF$_4$ to be mentioned below, as well as [Cu(dppb)(DPEPhos)]BF$_4$, [Cu(μ-1)dppb]$_2$, [Cu(μ-Cl)DPEphos]$_2$, Cu(2-tzq)(DPEPhos), [Cu(PNP)]$_2$, compound 1001, Cu(Bpz$_4$)(DPEPhos), etc.; Pt complexes such as FPt, Pt-4, etc. Their structures are shown below.

[Chem. 50]

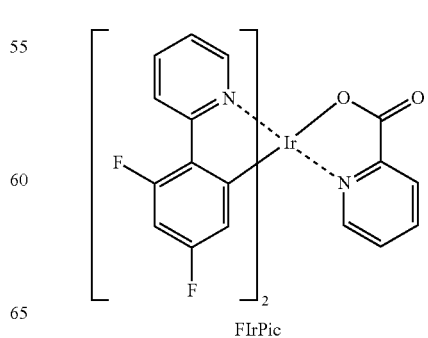
FIrPic

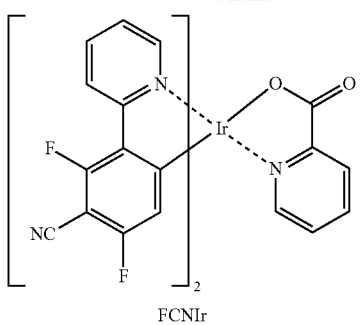
FCNIr
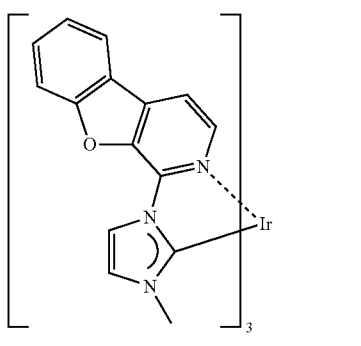
Ir(dbfml)
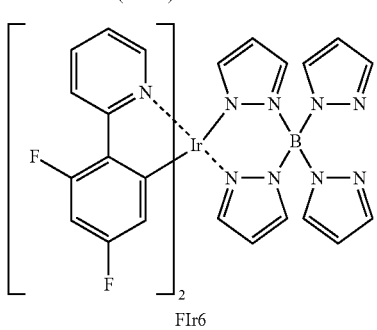
FIr6
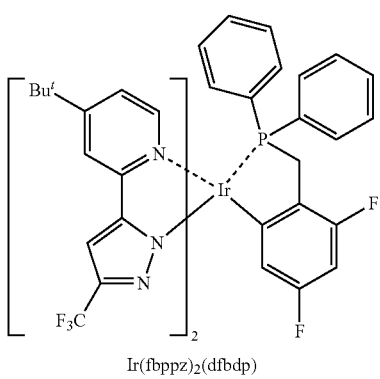
Ir(fbppz)$_2$(dfbdp)
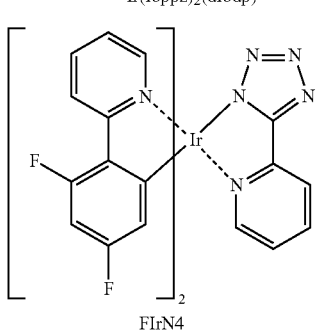
FIrN4
[Chem. 51]
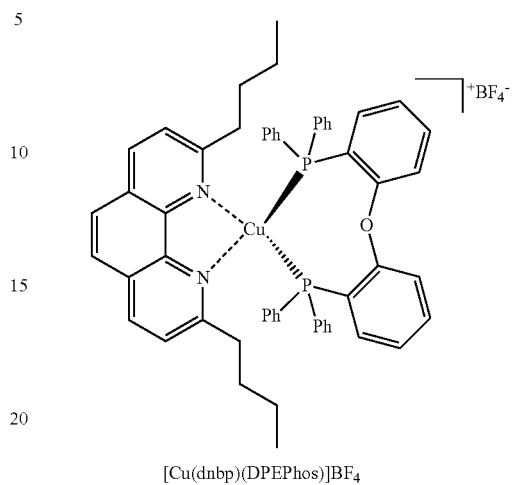
[Cu(dnbp)(DPEPhos)]BF$_4$
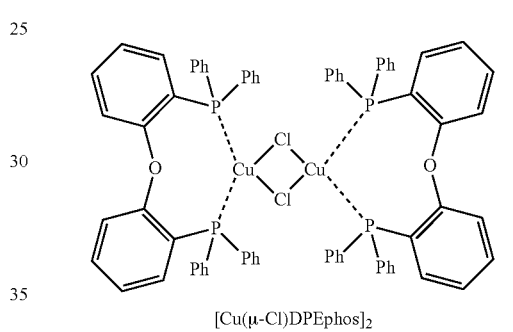
[Cu(μ-Cl)DPEphos]$_2$
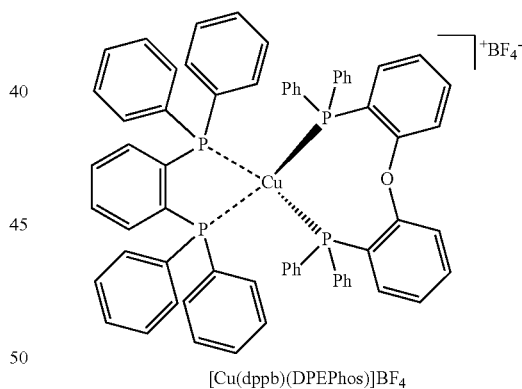
[Cu(dppb)(DPEPhos)]BF$_4$
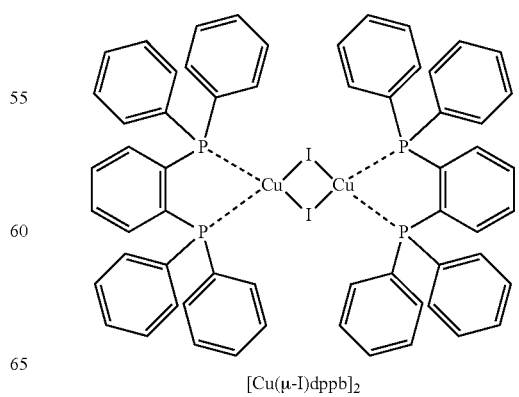
[Cu(μ-I)dppb]$_2$ -continued

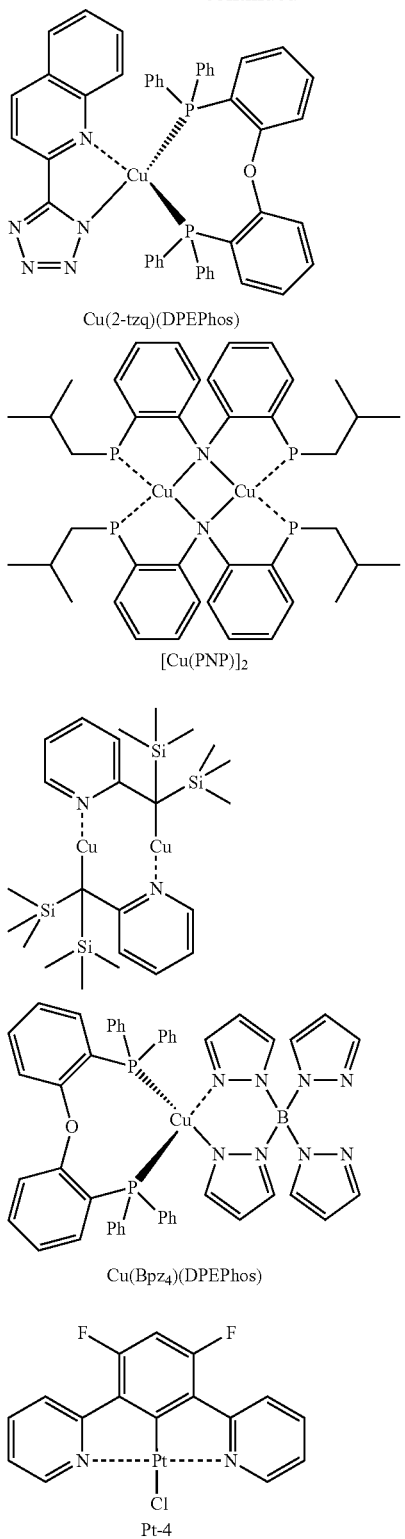

Cu(2-tzq)(DPEPhos)

[Cu(PNP)]₂ compound 1001

Cu(Bpz₄)(DPEPhos)

[Chem. 52]

Pt-4

Typical phosphorescent materials are mentioned above; however, the phosphorescent materials usable in the invention are not limited to these. For example, the materials described in CMC Publishing's "Device Physics, Material Chemistry, and Device Application of Organic Light Emitting Diodes", Chap. 9 are also usable here.

Preferred examples of the thermal activation-type delayed fluorescent materials include, for example, the following PIC-TRZ and [Cu(PNP-$^t$Bu)]₂.

[Chem. 53]

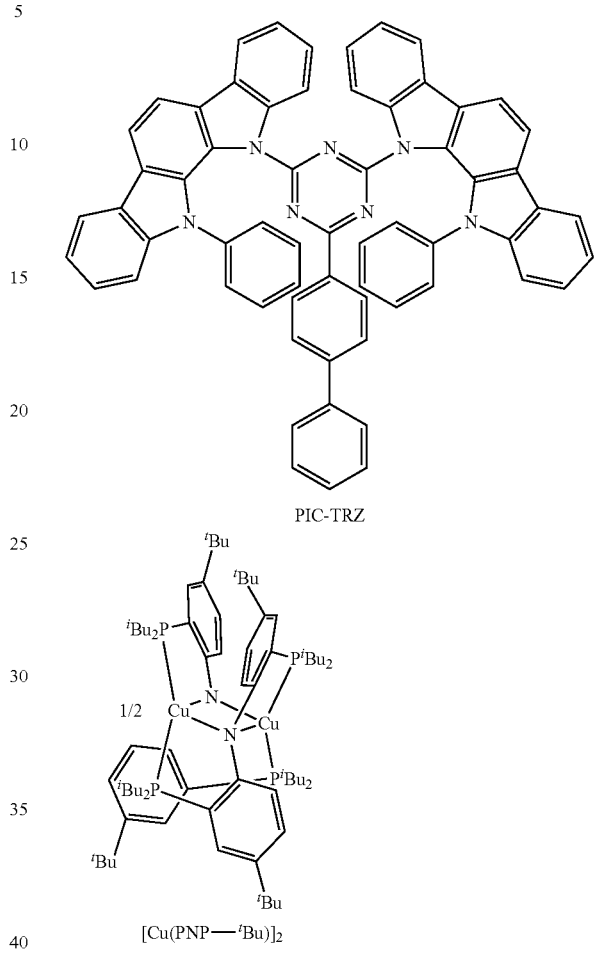

PIC-TRZ

[Cu(PNP—$^t$Bu)]₂

Preferred examples of the exciplex-type light-emitting materials include, for example, the following m-MTDATA and PBD, PyPySPyPy and NPB, and PPSPP and NPB.

[Chem. 54]

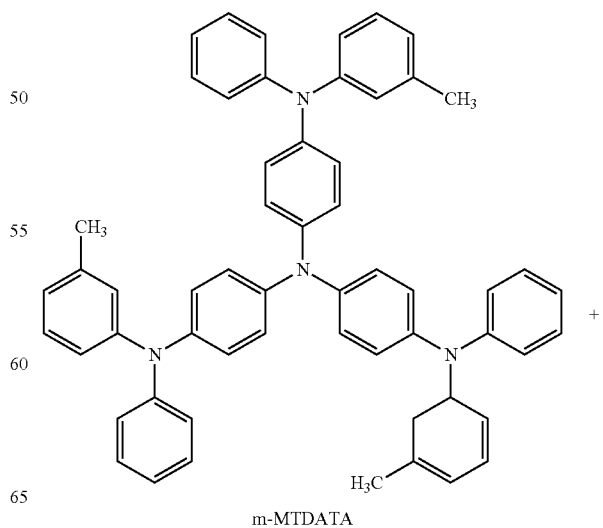

m-MTDATA

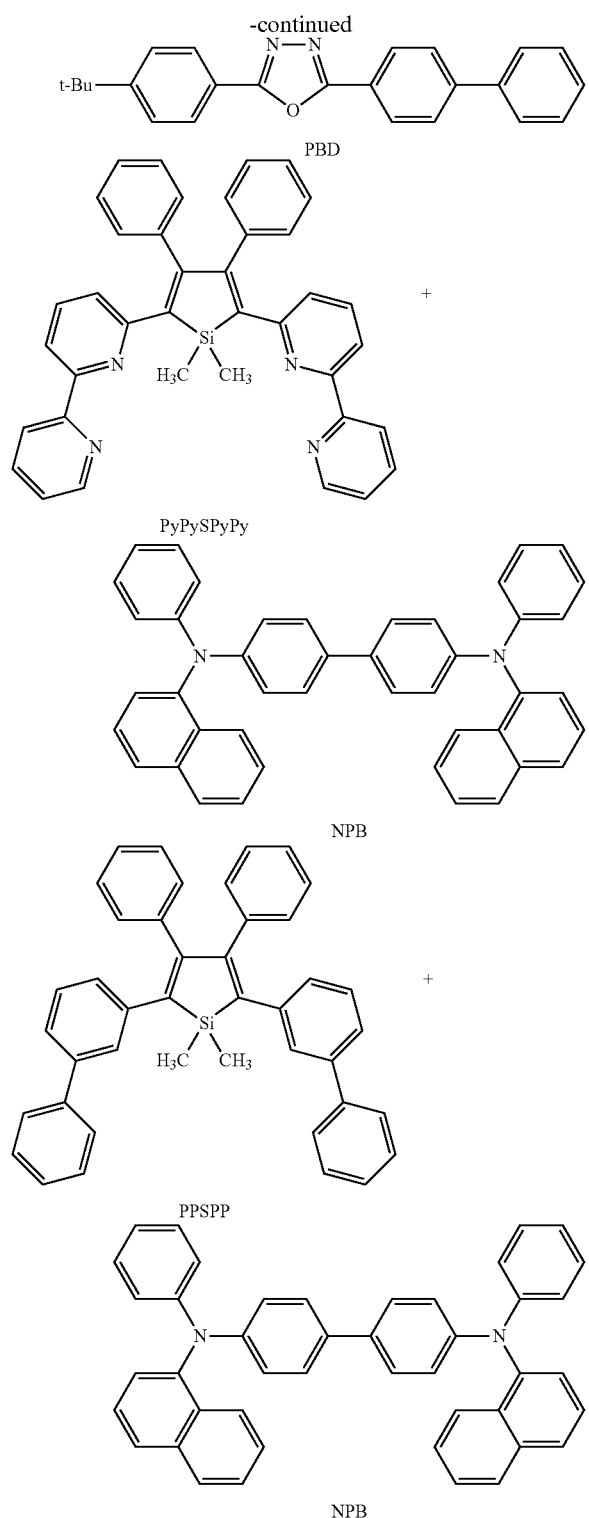

Between the second organic material and the cathode, preferably inserted is a layer formed of a known hole-blocking material. In producing the constitutive layers and the electrodes constituting the organic electroluminescence element, any known production method may be suitably selected and employed. In addition, known techniques as well as various modifications easily derived from known techniques may be optionally applied to the organic electroluminescence-element of the invention.

[Organic Thin-Film Solar Cell]

The compounds represented by the general formula (1) can also be effectively used in organic thin-film solar cells.

A typical organic thin-film solar cell is so configured that an anode of ITO or the like, a hole transport layer, a photoelectric conversion layer, an electron transport layer and a cathode are laminated on a transparent substrate of glass or the like. The photoelectric conversion layer has a p-type semiconductor layer on the anode side and has an n-type semiconductor layer on the cathode side. The compound represented by the general formula (1) can be used as a material of those hole transport layer, p-type semiconductor layer, n-type semiconductor layer and electron transport layer, depending on the physical properties thereof. The compound represented by the general formula (1) can function as a hole transport material or an electron transport material in the organic thin-film solar cell.

The organic thin-film solar cell using the compound represented by the general formula (1) may be optionally provided with a hole blocking layer, an electron blocking layer, an electron injection layer, a hole injection layer, a planarization layer and the like, in addition to the above. In the organic thin-film solar cell using the compound represented by the general formula (1), known materials used in organic thin-film solar cells can be suitably selected and combined. If desired, known techniques as well as various modifications that may be readily derived from known techniques may be given to the organic thin-film solar cell using the compound of the invention.

The other materials constituting the organic electroluminescence element of the invention may be suitably selected from known materials and may be optimized. For example, a hole injection layer is preferably arranged between the anode and the first organic layer as mentioned above, and as the material constituting the hole injection material, preferably used are poly(ethylenedioxy)thiophene (PEDOT), metal oxides such as molybdenum oxide, etc., and known aniline derivatives.

EXAMPLES

The characteristics of the invention are described more concretely with reference to the following Synthesis Examples, Test Examples and Production Examples. In the following Examples, the materials used, the details of the treatment and the treatment process may be suitably modified or changed not overstepping the spirit and the scope of the invention. Accordingly, the scope of the invention should not be limitatively interpreted by the Examples mentioned below.

Synthesis Example 1

Compound 9 was synthesized according to the following scheme in this Synthesis Example.

[Chem. 55]

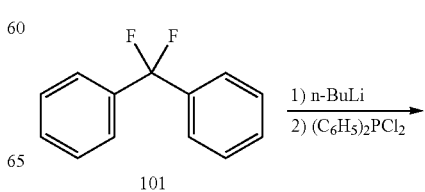

-continued

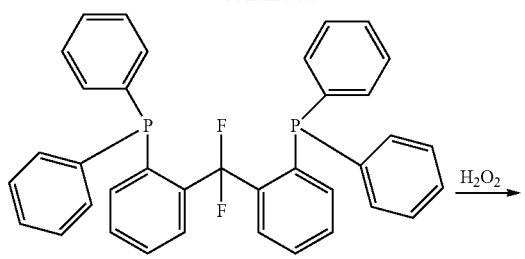
102

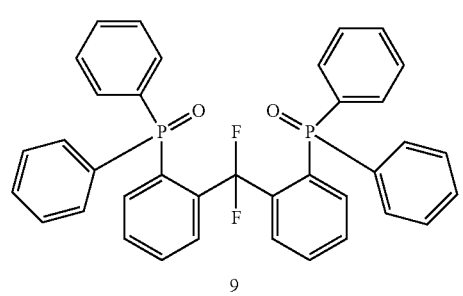
9

Compound 101 and n-butyllithium were reacted at −80° C. for 2 hours, and then $(C_6H_5)_2PCl$ was added thereto and further reacted at −80° C. for 2 hours. The resulting compound 102 was reacted with hydrogen peroxide for 1 hour, then purified through column chromatography using ethyl acetate as an eluent, and recrystallized in chloroform/ether to give the compound 9 as a white crystal (yield 70%).

Synthesis Example 2

Compound 13 was synthesized according to the following scheme in this Synthesis Example.

[Chem. 56]

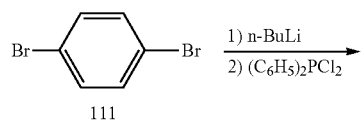
111

-continued

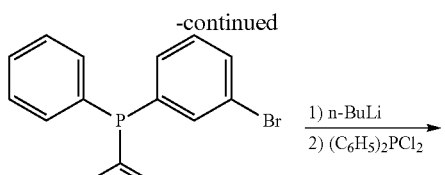
112

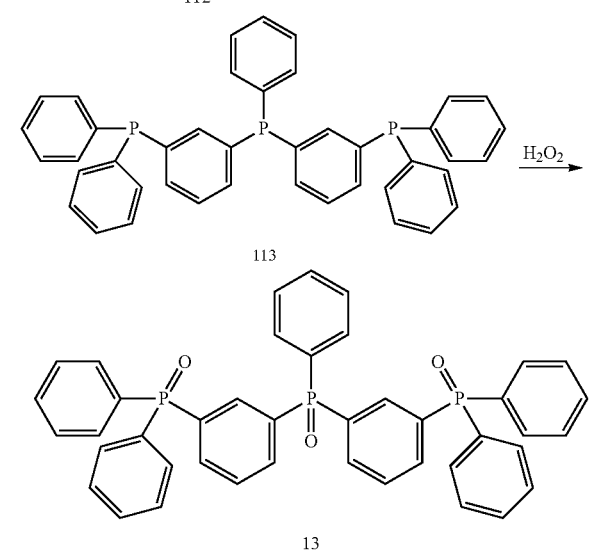
113

Compound 111 and n-butyllithium were reacted at −80° C. for 2 hours, and then $(C_6H_5)_2PCl$ was added thereto and further reacted at −80° C. for 2 hours. The resulting compound 112 was reacted with n-butyllithium at −80° C. for 2 hours, and then $(C_6H_5)_2PCl$ was added thereto and further reacted at −80° C. for 2 hours. The resulting compound 113 was reacted with hydrogen peroxide for 1 hour, then purified through column chromatography using ethyl acetate as an eluent, and recrystallized in chloroform/ether to give the compound 13 as a white crystal (yield 35%).

Synthesis Example 3

Compound 15 was synthesized according to the following scheme in this Synthesis Example.

[Chem. 57]

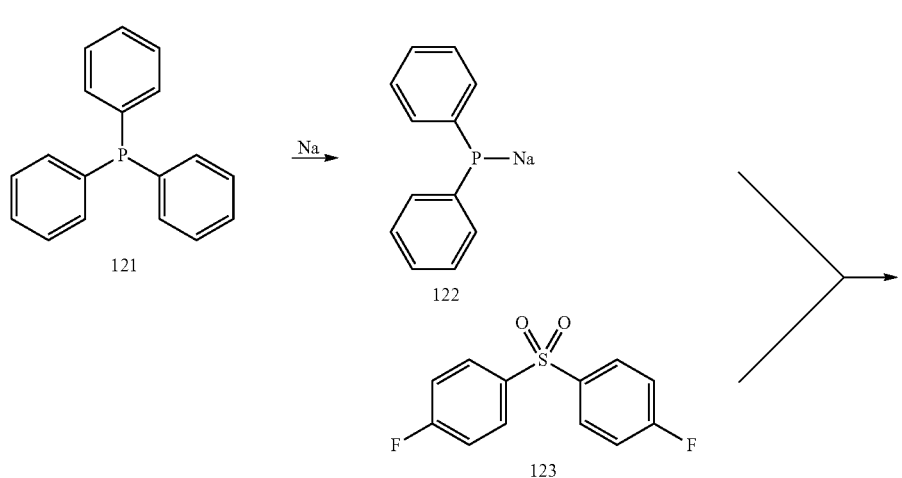

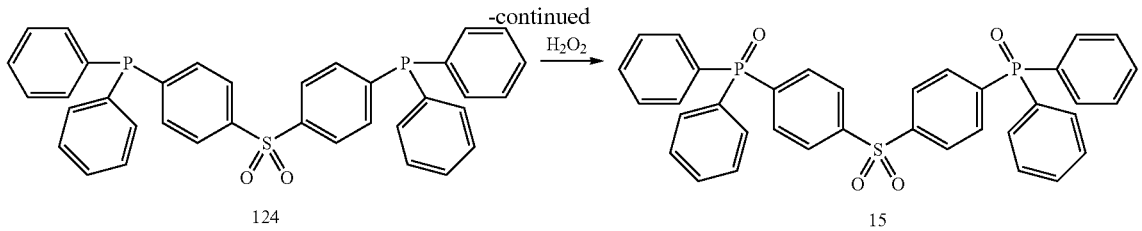

In THF, compound 121 was reacted with metal sodium at −80° C. The resulting compound 112 was mixed with compound 123, and reacted at −80° C. for 12 hours in THF. The resulting compound 124 was reacted with hydrogen peroxide for 1 hour, then purified through column chromatography using ethyl acetate/methanol (100/4) as an eluent, and recrystallized in ethyl acetate/ether to give the compound 15 as a transparent crystal (yield 54%).

Synthesis Example 4

Compounds 1 to 8, 10 to 12, 14, 16 to 18 were synthesized in the same manner as in Synthesis Examples 1 to 3.

Test Example 1

In this Test Example, the lowest excited triplet energy level at 77° K of the compounds 1 to 18 synthesized in Synthesis Examples 1 to 4 was measured.

Each compound was deposited on a quartz substrate in a mode of vacuum evaporation thereon to form a thin film of the compound having a thickness of from 100 to 200 nm. The sample was cooled at 77° K, and the PL spectrum thereof was measured. The energy at the peak value on the shortest wavelength side of the PL spectrum was calculated to be the lowest excited triplet energy level of the compound.

The results are shown in Table 1 below.

Production Example 1

In this Production Example, various compounds were used in producing organic electroluminescence elements each having the configuration shown in FIG. 1, and the luminescent efficiency thereof was evaluated.
(1) Production of Organic Electroluminescence Element On glass 1, a film of indium/tin oxide (ITO) 2 was formed in a thickness of from about 30 to 100 nm, and a film of poly(ethylenedioxy)thiophene (PEDOT) 3 was formed thereon in a thickness of 30 nm. Next, PYD2 (first organic material) doped with 10% by weight of any one light-emitting material of [Cu(dnbp)(DPEPhos)]BF$_4$, [Cu(μ-1)dppb]$_2$ or FIrPic was dissolved in an organic solvent and applied to the above in a mode of spin coating, thereby forming a first organic layer 4 in a thickness of 30 nm. Further on the above, a second organic material of any one of BPhen, TPBI, TmPyPB, SPPO1, TSPO1, PO15, compound 2 or compound 15 having the structure mentioned below was deposited in a mode of vacuum evaporation to thereby form a second organic layer 5 having a thickness of 50 nm. Next, lithium fluoride (LiF) 6 was deposited on the above in a mode of vapor deposition in a thickness of 0.5 nm, and thereafter aluminium (Al) 7 was vapor-deposited thereon in a thickness of 100 nm, thereby producing an organic electroluminescence element having the layer configuration shown in FIG. 1.

(2) Evaluation of Luminescent Efficiency

Using a semiconductor parameter analyzer and a power meter, the current-voltage-luminance (J-V-L) characteristic of the organic electroluminescence element produced in the above (1) was measured. The EL spectrum was measured using a multichannel spectroscope. From these results, the quantum efficiency was calculated.

Figure 2:
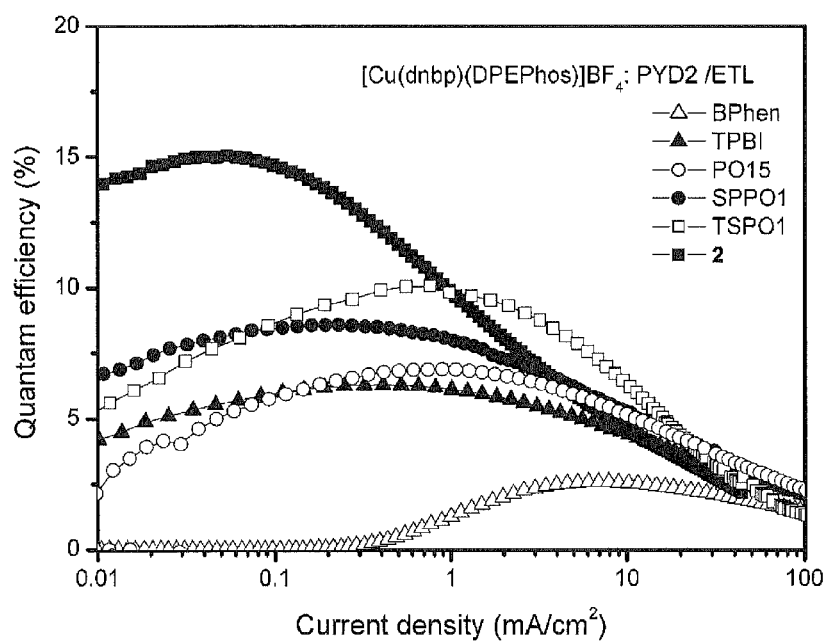
[FIG. 2] This is a graph showing the relationship between the current density and the quantum efficiency in Production Example 1.
Figure 3:
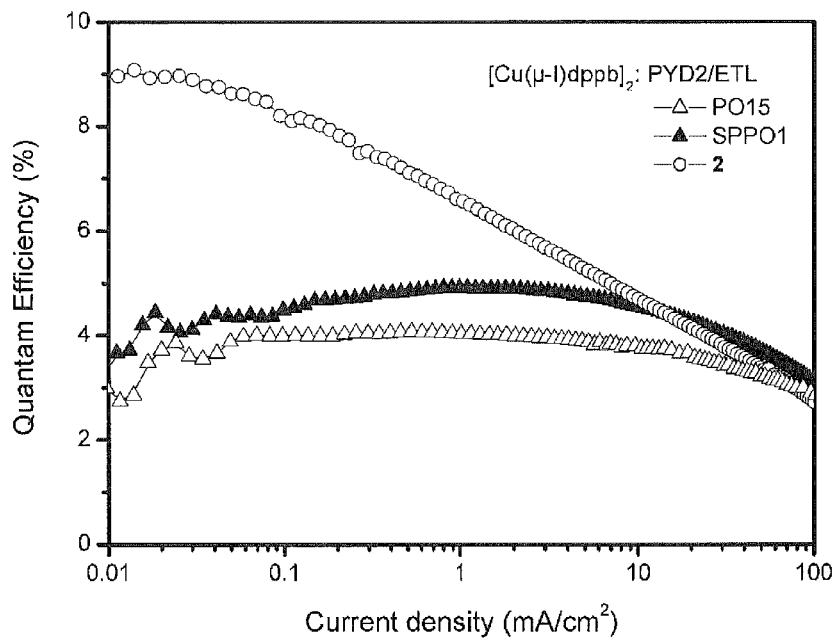
[FIG. 3] This is another graph showing the relationship between the current density and the quantum efficiency in Production Example 1.
Figure 4:
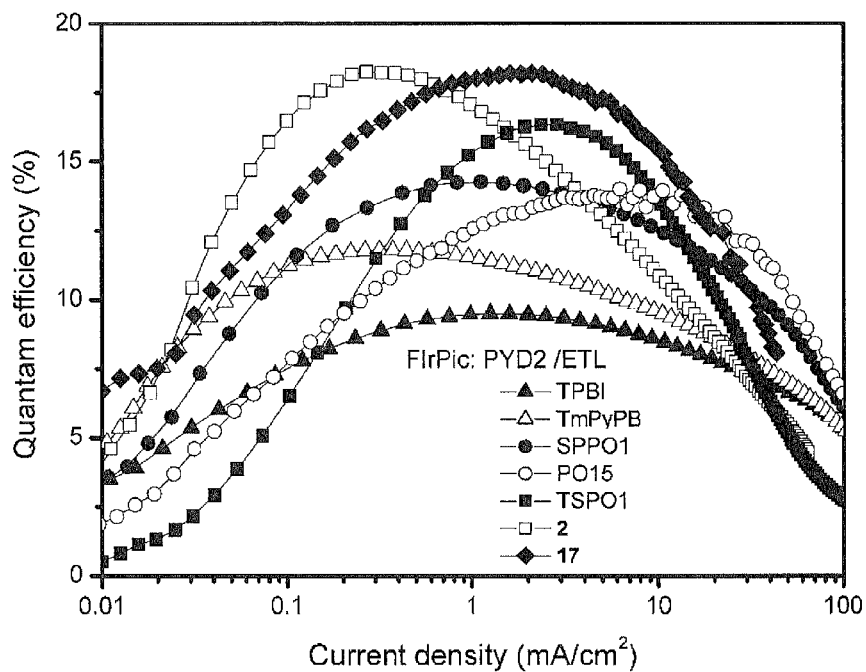
[FIG. 4] This is still another graph showing the relationship between the current density and the quantum efficiency in Production Example 1.

FIGS. 2 to 4 show the results. In the case where a phosphorescent material FIrPic was used as the light-emitting material and the compound 2 or the compound 15 was used as the second organic material, an extremely high quantum efficiency of 18% was obtained. In addition, in the case where a Cu complex [Cu(dnbp)(DPEPhos)]BF$_4$ was used as the light-emitting material and the compound 2 was used as the second organic material, a high quantum efficiency or more than 15% was obtained.

In the same manner as above but using CzSi, PO12, mCP, SimCP, SimCP2, CBPE or CBZ as the first organic material in place of PYD2, organic electroluminescence elements were produced and the luminescent efficiency thereof was evaluated. As a result, the samples using the compound of the invention as the second organic material provided a high luminescent efficiency.

Production Example 2

In this Production Example, the organic layer to which the light-emitting material is to be added was varied to produce different organic electroluminescence elements, and the luminescent efficiency thereof was evaluated.

According to the production method of Production Example 1, a film of indium/tin oxide (ITO) 2, a film of poly(ethylenedioxy)thiophene (PEDOT) 3, a first organic layer 4 of FIrPic-doped PYD2, a second organic layer 5 of compound 2, a film of lithium fluoride (LiF) 6 and a film of aluminium (Al) 7 were formed on glass 1 each in the same thickness as in Production Example 1, thereby giving a device I.

A device II was produced in the same manner as that for the device I, except that the layer to be doped with FIrPic was changed from the first organic layer to the second organic layer.

A device III was produced in the same manner as that for the device I, except that both the first organic layer and the second organic layer were doped with FIrPic.

Figure 5:
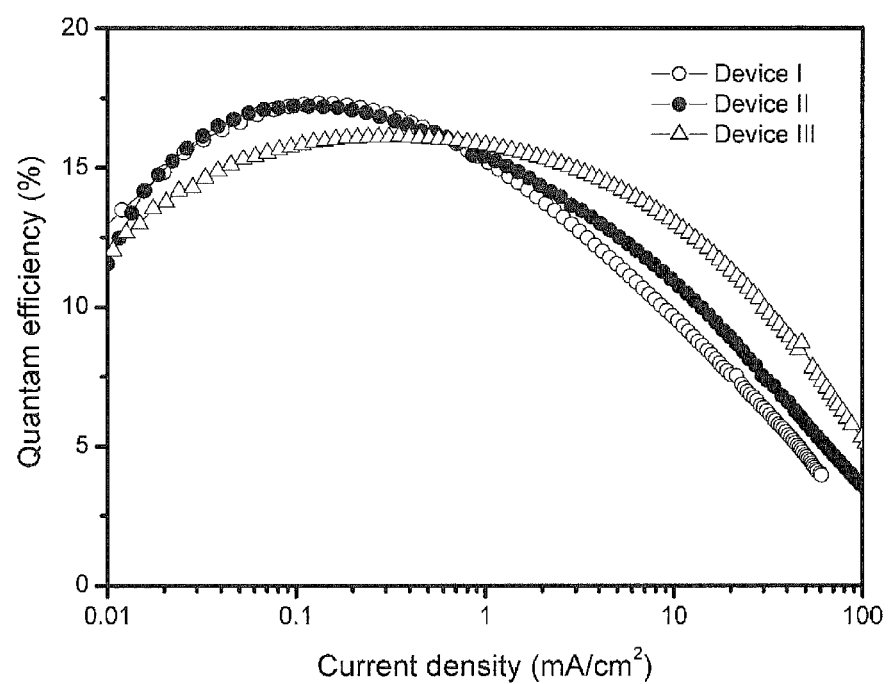
[FIG. 5] This is a graph showing the relationship between the current density and the quantum efficiency in Production Example 2.

The luminescent efficiency of each device was evaluated in the same manner as in Production Example 1, and the results are shown in FIG. 5.

Every device provided a high quantum efficiency of more than 15%. In particular, the device I in which the first organic layer alone was doped with the light-emitting material and the device II in which the second organic layer alone was doped with the light-emitting material provided a markedly high quantum efficiency.

Production Example 3

In this Production Example, the compounds 1 to 16 synthesized in Synthesis Example were used to produce organic electroluminescence elements, and the quantum efficiency thereof was measured.

On glass 1, a film of indium/tin oxide (ITO) 2 was formed in a thickness of from about 30 to 100 nm, and a film of poly(ethylenedioxy)thiophene (PEDOT) 3 was formed thereon in a thickness of 40 nm. Next, PYD2 (first organic material) doped with 10% by weight of any one light-emitting material of FIrPic or [Cu(dnbp)(DPEPhos)]⁺ was dissolved in an organic solvent and applied to the above in a mode of spin coating, thereby forming a first organic layer 4 in a thickness of 30 nm. Further on the above, a second organic material shown in Table 1 was deposited in a mode of vacuum evaporation to thereby form a second organic layer 5 having a thickness of 50 nm. Next, lithium fluoride (LiF) 6 was deposited on the above in a mode of vapor deposition in a thickness of 0.7 nm, and thereafter aluminium (Al) 7 was vapor-deposited thereon in a thickness of 100 nm, thereby producing an organic electroluminescence element having the layer configuration shown in FIG. 1. In the same manner as in Production Example 1, the quantum efficiency was measured, and the results are shown in Table 1.

TABLE 1

| Second Organic Material | $T_1$ (eV) | Quantum Efficiency $EQE_{max}$ (%) | |
|---|---|---|---|
| | | FIrPic | [Cu(dnbp)(DPEphos)]⁺ |
| Compound 1 | 3.05 | 18 | 15 |
| Compound 2 | 3.05 | 18 | 15 |
| Compound 3 | 3.03 | 18 | 15 |
| Compound 4 | 3.05 | 18 | 13 |
| Compound 5 | 3.03 | 18 | 14 |
| Compound 6 | 3.00 | 17 | 11 |
| Compound 7 | 3.00 | 17 | 12 |
| Compound 8 | 2.95 | 16 | 9 |
| Compound 9 | 2.85 | 14 | 8 |
| Compound 10 | 3.05 | 18 | 13 |
| Compound 11 | 3.00 | 17 | 10 |
| Compound 12 | 2.95 | 16 | 9 |
| Compound 13 | 2.95 | 16 | 9 |
| Compound 14 | 2.85 | 14 | 8 |
| Compound 15 | 3.05 | 18 | 15 |
| Compound 16 | 3.05 | 17 | 13 |

As obvious from the results in Table 1, the organic electroluminescence elements produced by the use of any of the compounds 1 to 16 of the invention all attained a high luminescent efficiency.

INDUSTRIAL APPLICABILITY

The compounds of the invention are novel compounds having excellent characteristics as a charge transport material. Accordingly, the compounds of the invention are applicable to various organic devices. For example, the compounds are expected to be applicable to the field of display elements such as organic electroluminescence elements and the like, as well as other displays, backlights, electronic photographs, light sources for illuminations, light sources for photoexposure, light sources for reading, marks, signs, and interiors. In particular, the organic electroluminescence element using the compound of the invention as a delayed fluorescent material has a high luminescent efficiency. Accordingly, the invention has significant industrial applicability.

REFERENCE SIGNS LIST

1 Glass
2 ITO
3 PEDOT
4 First Organic Layer
5 Second Organic Layer
6 LiF
7 Al

The invention claimed is:

1. A compound represented by the following general formula (1):

General Formula (1)

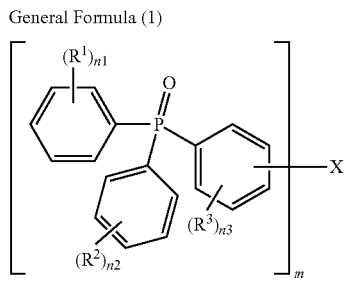

wherein $R^1$, $R^2$ and $R^3$ each independently represent a substituent, n1 and n2 each independently indicate an integer of from 0 to 5, n3 indicates an integer of from 0 to 4, X represents a linking group having any of the following structures, m is equal to the valence of the linking group X and indicates an integer of from 2 to 4;

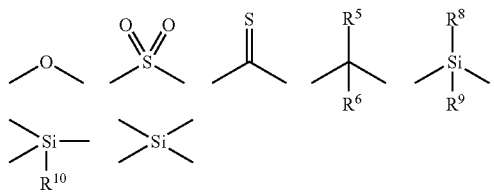

wherein $R^5$ and $R^6$ each independently represent a hydrogen atom, a halogen atom, a substituted or unsubstituted alkyl group, or a substituted or unsubstituted aryl group; $R^8$, $R^9$ and $R^{10}$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group; provided that when X is —O—, this links at the 3,3'-positions of the triphenylphosphine oxide structure of the general formula (1).

2. A compound according to claim 1, which is represented by the following general formula (2):

General Formula (2)

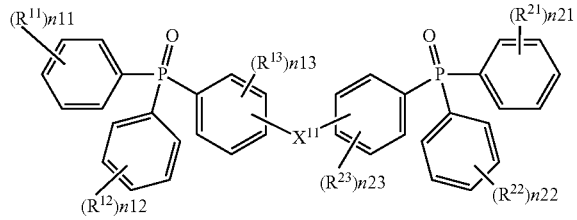

wherein $R^{11}, R^{12}, R^{13}, R^{21}, R^{22}$ and $R^{23}$ each independently represent a substituent, n11, n12, n21 and n22 each independently indicate an integer of from 0 to 5, n13 and n23 each independently indicate an integer of from 0 to 4, $X^{11}$ represents a linking group having any of the following structures;

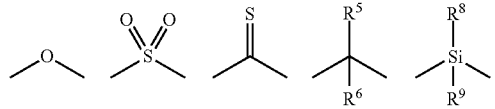

wherein $R^5$ and $R^6$ each independently represent a hydrogen atom, a halogen atom, a substituted or unsubstituted alkyl group, or a substituted or unsubstituted aryl group; $R^8$ and $R^9$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group; provided that when X is —O—, this links at the 3,3'-positions of the triphenylphosphine oxide structure of the general formula (1).

3. A compound according to claim 1, which is represented by the following general formula (2-1):

General Formula (2-1)

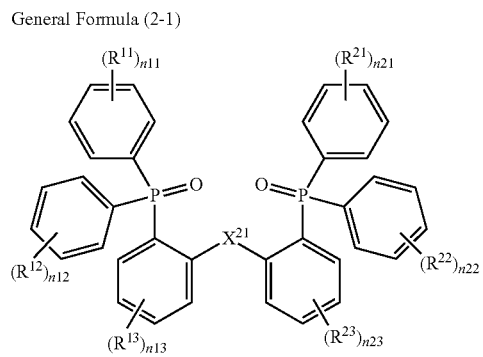

wherein $R^{11}, R^{12}, R^{13}, R^{21}, R^{22}$ and $R^{23}$ each independently represent a substituent, n11, n12, n21 and n22 each independently indicate an integer of from 0 to 5, n13 and n23 each independently indicate an integer of from 0 to 4, $X^{21}$ represents a linking group having any of the following structures;

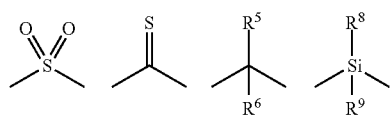

wherein $R^5$ and $R^6$ each independently represent a hydrogen atom, a halogen atom, a substituted or unsubstituted alkyl group, or a substituted or unsubstituted aryl group; $R^8$ and $R^9$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group.

4. A compound according to claim 1, which is represented by the following general formula (2-2):

General Formula (2-2)

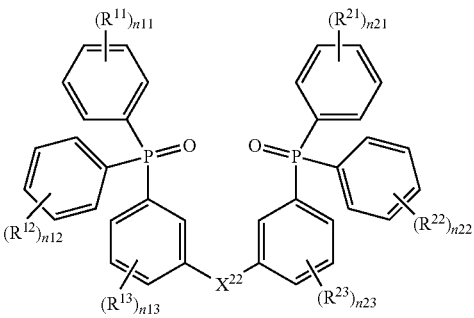

wherein $R^{11}, R^{12}, R^{13}, R^{21}, R^{22}$ and $R^{23}$ each independently represent a substituent, n11, n12, n21 and n22 each independently indicate an integer of from 0 to 5, n13 and n23 each independently indicate an integer of from 0 to 4, $X^{22}$ represents a linking group having any of the following structures;

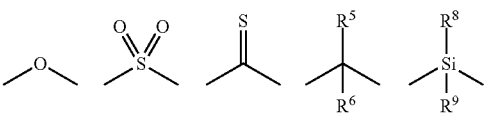

wherein $R^5$ and $R^6$ each independently represent a hydrogen atom, a halogen atom, a substituted or unsubstituted alkyl group, or a substituted or unsubstituted aryl group; $R^8$ and $R^9$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group.

5. A compound according to claim 1, which is represented by the following general formula (2-3):

General Formula (2-3)

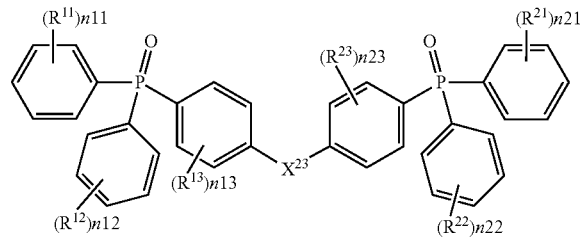

wherein $R^{11}, R^{12}, R^{13}, R^{21}, R^{22}$ and $R^{23}$ each independently represent a substituent, n11, n12, n21 and n22 each independently indicate an integer of from 0 to 5, n13 and n23 each independently indicate an integer of from 0 to 4, $X^{23}$ represents a linking group having any of the following structures;

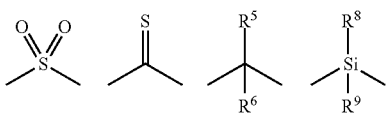

wherein $R^5$ and $R^6$ each independently represent a hydrogen atom, a halogen atom, a substituted or unsubstituted alkyl group, or a substituted or unsubstituted aryl group; $R^8$ and $R^9$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group.

6. The compound according to claim 1, wherein the linking group has the following structure

7. The compound according to claim 1, wherein the linking group has the following structure

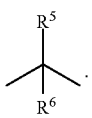

8. The compound according to claim 1, which has a lowest excited triplet energy level at 77°K of not lower than 2.80 eV.

9. The compound according to claim 1, which has a lowest excited triplet energy level at 77°K of not lower than 2.95 eV.

10. A charge transport material comprising a compound represented by the following formula (1):

General Formula (1)

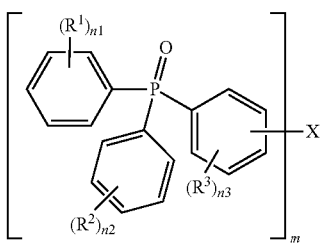

wherein $R^1$, $R^2$ and $R^3$ each independently represent a substituent, n1 and n2 each independently indicate an integer of from 0 to 5, n3 indicates an integer of from 0 to 4, X represents a linking group having any of the following structures, m is equal to the valence of the linking group X and indicates an integer of from 2 to 4;

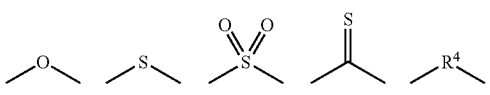

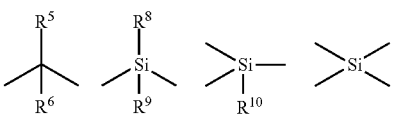

wherein $R^4$ represents a substituted or unsubstituted aliphatic cyclic linking group; $R^5$ and $R^6$ each independently represent a hydrogen atom, a halogen atom, a substituted or unsubstituted alkyl group, or a substituted or unsubstituted aryl group; $R^8$, $R^9$ and $R^{10}$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group; provided that when X is —O—, this links at the 3,3'-positions of the triphenylphosphine oxide structure of the general formula (1).

11. An organic device using a compound represented by the following formula (1):

General Formula (1)

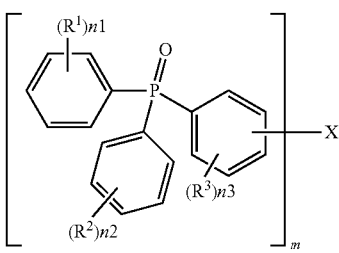

wherein $R^1$, $R^2$ and $R^3$ each independently represent a substituent, n1 and n2 each independently indicate an integer of from 0 to 5, n3 indicates an integer of from 0 to 4, X represents a linking group having any of the following structures, m is equal to the valence of the linking group X and indicates an integer of from 2 to 4;

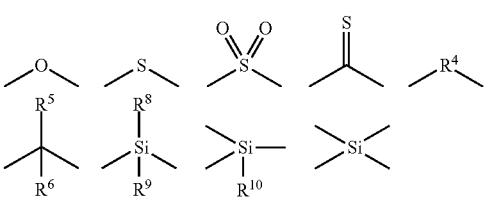

wherein $R^4$ represents a substituted or unsubstituted aliphatic cyclic linking group; $R^5$ and $R^6$ each independently represent a hydrogen atom, a halogen atom, a substituted or unsubstituted alkyl group, or a substituted or unsubstituted aryl group; $R^8$, $R^9$ and $R^{10}$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group; provided that when X is —O—, this links at the 3,3'-positions of the triphenylphosphine oxide structure of the general formula (1).

12. An organic electroluminescence element using a compound represented by the following formula (1):

General Formula (1)

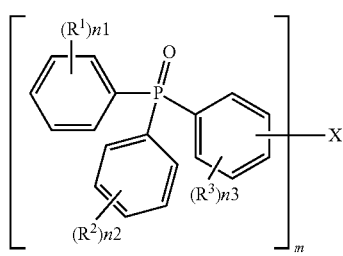

wherein $R^1$, $R^2$ and $R^3$ each independently represent a substituent, n1 and n2 each independently indicate an integer of from 0 to 5, n3 indicates an integer of from 0 to 4, X represents a linking group having any of the following structures, m is equal to the valence of the linking group X and indicates an integer of from 2 to 4;

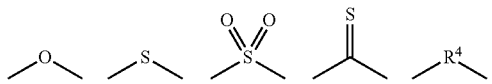

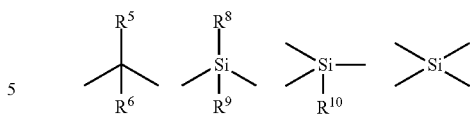

wherein $R^4$ represents a substituted or unsubstituted aliphatic cyclic linking group; $R^5$ and $R^6$ each independently represent a hydrogen atom, a halogen atom, a substituted or unsubstituted alkyl group, or a substituted or unsubstituted aryl group; $R^8$, $R^9$ and $R^{10}$ each independently represent a hydrogen atom, a substituted or unsubstituted alkyl group, or a substituted or unsubstituted aryl group; at least one of $R^8$ and $R^9$ is a hydrogen atom, or a substituted or unsubstituted alkyl group; provided that when X is —O—, this links at the 3,3'-positions of the triphenylphosphine oxide structure of the general formula (1).

\* \* \* \* \*